(12) United States Patent
Wolfe et al.

(10) Patent No.: US 10,646,237 B2
(45) Date of Patent: May 12, 2020

(54) ASSOCIATED INSTRUMENTS AND METHODS FOR POSTERIOR STABILIZED KNEE PREPARATION

(71) Applicant: Biomet Manufacturing, LLC, Warsaw, IN (US)

(72) Inventors: Alexander P. Wolfe, Fort Wayne, IN (US); Duke A. Fox, Warsaw, IN (US); Nicholas William Hutchison, Chippenham (GB)

(73) Assignee: Biomet Manufacturing, LLC, Warsaw, IN (US)

( * ) Notice: Subject to any disclaimer, the term of this patent is extended or adjusted under 35 U.S.C. 154(b) by 554 days.

(21) Appl. No.: 15/375,914

(22) Filed: Dec. 12, 2016

(65) Prior Publication Data

US 2017/0164959 A1    Jun. 15, 2017

Related U.S. Application Data

(60) Provisional application No. 62/267,456, filed on Dec. 15, 2015.

(51) Int. Cl.
   *A61B 17/56*    (2006.01)
   *A61B 17/58*    (2006.01)
   (Continued)

(52) U.S. Cl.
   CPC ...... *A61B 17/1764* (2013.01); *A61B 17/1675* (2013.01)

(58) Field of Classification Search
   CPC ............ A61B 17/1764; A61B 17/1675; A61B 17/1637; A61B 17/1662; A61B 17/17;
   (Continued)

(56) References Cited

U.S. PATENT DOCUMENTS 5,569,259 A    10/1996  Ferrante et al.
5,716,360 A *   2/1998  Baldwin ............ A61B 17/1677
                                          606/79
(Continued)

OTHER PUBLICATIONS

"Vanguard Global Total Knee Instrumentaion", BIOMET—Surgical Technique, (2015), 48 pgs.

*Primary Examiner* — Jessica Weiss
(74) *Attorney, Agent, or Firm* — Schwegman Lundberg & Woessner, P.A.

(57) ABSTRACT

Methods, systems and apparatuses including an orthopedic assembly are disclosed. The orthopedic assembly can include a femoral component and a guide. The femoral component can be configured to engage a resected distal surface of a femur. The femoral component can have a box cutout configured to provide access to a distal centrally located region of the femur. The box cutout can be disposed between a medial condyle, a lateral condyle and an anterior portion of the femoral component. The guide can be configured to selectively connect to the femoral component at one or more locations and can be spaced from the femur. The guide can have an opening therethrough configured to provide access to the box cutout and the distal centrally located region of the femur. One or more surfaces of the guide can define the opening, each of the one or more surfaces can be configured to act as a guide surface.

17 Claims, 23 Drawing Sheets

(51) Int. Cl.
*A61F 2/36* (2006.01)
*A61B 17/17* (2006.01)
*A61B 17/16* (2006.01)

(58) Field of Classification Search
CPC ............ A61B 17/1732; A61B 17/1735; A61B 17/1739
USPC ........ 606/79–85, 86 R, 87–89, 99–100, 104; 623/20.35
See application file for complete search history.

(56) References Cited

U.S. PATENT DOCUMENTS

| | | |
|---|---|---|
| 8,758,356 B2 | 6/2014 | Fearon et al. |
| 8,764,759 B2 | 7/2014 | Dees, Jr. |
| 8,771,280 B2 | 7/2014 | Bailey et al. |
| 2009/0149964 A1* | 6/2009 | May ................... A61B 17/155 623/20.15 |
| 2011/0213378 A1* | 9/2011 | Dees, Jr. ............ A61B 17/1675 606/89 |
| 2011/0218541 A1* | 9/2011 | Bailey ................ A61B 17/56 606/88 |
| 2011/0307067 A1 | 12/2011 | Dees |

* cited by examiner

ASSOCIATED INSTRUMENTS AND METHODS FOR POSTERIOR STABILIZED KNEE PREPARATION

CLAIM OF PRIORITY

This application claims the benefit of U.S. Provisional Patent Application Ser. No. 62/267,456, filed on Dec. 15, 2015, the benefit of priority of which is claimed hereby, and which is incorporated by reference herein in its entirety.

FIELD

The present subject matter relates to orthopedic procedures and, more particularly, to femoral components and associated apparatuses and methods for performing bone and/or soft tissue removal during knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Guides and other instruments are used to guide the removal of bone, for example, to form resected surfaces.

Prostheses are placed on the resected surfaces and used to replicate the articular surfaces. Knee prostheses can include a femoral implant inserted on the distal end of the femur, which articulates with a tibial implant inserted on the proximal end of a tibia to replicate the function of a healthy natural knee.

Various types of arthroplasties are known including a total knee arthroplasty (TKA), where all of the articulating compartments of the joint are repaired with prosthetic components. For a TKA it may also be necessary during the knee arthroplasty procedure to sacrifice certain ligaments of the knee joint, such as the posterior cruciate ligament (PCL). In those cases, the prosthetic knee components may also be designed to simulate the behavior of the sacrificed ligament. For example, if the PCL is sacrificed, the prosthetic femoral implant and the prosthetic tibial implant may be stabilized posteriorly to resist posterior translation of the prosthetic tibial implant relative to the prosthetic femoral implant.

OVERVIEW

The present inventors recognize, among other things, an opportunity for reducing surgical complexity and time spent in the resection of portions the femur. More particularly, the present inventors have recognized that in posterior stabilized knee arthroplasties, a recess in the femur can be created with a trial femoral component, a box guide and dedicated surgical instruments such as a trephine and/or a reamer. As such, the trephine and/or reamer can be used in tandem or alone to rapidly create the recess in the femur and eliminate the use of a saw blade and chisel. Elimination of the saw blade and chisel can reduce procedure time, and can additionally reduce the likelihood for surgical error. Furthermore, the present inventors have recognized that a single box guide can be used with a variety of differently sized femoral components. This can eliminate the need for multiple guides. According to some examples, the box guide and femoral component(s) can be configured with features that facilitate rapid coupling and decoupling there between.

To further illustrate the apparatuses, systems and methods disclosed herein, the following non-limiting examples are provided:

In Example 1, an orthopedic assembly can comprise a femoral component and a guide. The femoral component can be configured to engage a resected distal surface of a femur and can have a box cutout configured to provide access to a distal centrally located region of the femur. The box cutout can be disposed between a medial condyle, a lateral condyle and an anterior portion of the femoral component. The guide can be configured to selectively connect to the femoral component at one or more locations and spaced from the femur and can have an opening therethrough configured to provide access to the box cutout and the distal centrally located region of the femur. The one or more surfaces of the guide can define the opening. Each of the one or more surfaces can be configured to act as a guide surface.

In Example 2, the assembly of Example 1, wherein the guide can be configured as a frame to form the opening having both a first opening portion and a second opening portion, both the first opening portion and the second opening portion can allow access to the box cutout and the distal portion of the femur from different orientations.

In Example 3, the assembly of Example 2, wherein a proximal frame portion of the guide that forms the first opening portion can include a recessed lip configured to be engaged by a portion of a trephine, the trephine can be configured to cut tissue at the distal centrally located region of the femur.

In Example 4, the assembly of Example 3, wherein the recessed lip can set a desired access depth for the trephine.

In Example 5, the assembly of Example 2, wherein an anterior frame portion of the guide can form the second opening portion and can include at least one distal surface configured to act as a stop to set a desired access depth for a reamer.

In Example 6, the assembly of any one or any combination of Examples 1-5, wherein the one or more surfaces of the guide can comprise a first surface spaced by the opening from a second surface, and wherein a medial-lateral distance between and medial-lateral positioning of the first and the second surfaces can correspond to a medial-lateral distance and medial-lateral positioning of surfaces of the medial and the lateral condyles that form the box cutout.

In Example 7, the assembly of any one or any combination of Examples 1-6, wherein a proximal-distal extent of the first and second surfaces of the guide can exceed a proximal-distal extent of the box cutout.

In Example 8, the assembly of any one or any combination of Examples 1-7, wherein the one or more surfaces are configured to act as a track to be traced along by a reamer in removing one or more of bone and soft tissue from the distal centrally located region of the femur.

In Example 9, the assembly of any one or any combination of Examples 1-8, can further comprise a femoral insert that can be configured to be secured within the box cutout, together the femoral insert and the femoral component can form a trial femoral prosthesis after a desired amount of tissue in the distal centrally located region of the femur has been removed.

In Example 10, the assembly of any one or any combination of Examples 1-9, wherein the guide can selectively connect to the femoral component via a locking feature that can be biased into engagement with a mating recess through an aperture in the femoral component.

In Example 11, the assembly of any one or any combination of Examples 1-10, wherein a distal frame portion of the guide can define the opening, the distal frame portion can have at least one distal surface configured to act as a stop to set a desired access depth for a reamer.

In Example 12, a system for guiding femoral at least one of bone and tissue removal during a knee replacement surgery, the system can comprise a femoral component, a guide, and a first cutting tool. The femoral component can be configured to engage a resected distal surface of a femur and can have a box cutout configured to provide access to a distal centrally located region of the femur. The box cutout can be disposed between a medial condyle, a lateral condyle and an anterior portion of the femoral component. The guide can be configured to selectively connect to the femoral component at one or more locations. The guide can comprise a frame forming an enclosed opening configured to provide access to the box cutout and the distal centrally located region of the femur. The first cutting tool can have a distal section configured to access the box cutout and the distal centrally located region of the femur via the opening. The first cutting tool can have a second portion more proximally disposed than the first portion and can have a larger diameter than the first portion configured to contact the guide.

In Example 13, the system of Example 12, wherein the guide and first cutting tool can be configured such that insertion of the first cutting tool into the guide occurs until contact is made between the second portion and the guide. The contact can set a desired access depth for the first portion relative to the guide. The desired access depth can provide for removal of a desired amount of tissue in the distal centrally located region of the femur.

In Example 14, the system of any one or any combination of Examples 12-13, wherein the opening can have both a first opening portion and a second opening portion, both the first opening portion and the second opening portion can allow access to the box cutout and the distal portion of the femur from different orientations.

In Example 15, the system of Example 14, wherein the first cutting tool can comprise a trephine, and wherein a proximal frame portion of the guide that forms the first opening portion can include a recessed lip configured to be engaged by a portion of the trephine. The trephine can be configured to cut tissue at the distal centrally located region of the femur.

In Example 16, the system of Example 15, can further comprise a second cutting tool comprising a reamer. The reamer can be configured to cut tissue by one or both of plunging and milling, and the frame can form one or more surfaces that can be configured to act as a track to be traced along by the reamer when removing at least one of bone and tissue from the distal centrally located region of the femur.

In Example 17, the system of any one or any combination of Examples 12-16, wherein the first cutting tool can comprise a reamer. The reamer can be configured to cut tissue by one or both of plunging and milling, and the frame can form one or more surfaces that can be configured to act as a track to be traced along by the reamer when removing at least one of bone and tissue from the distal centrally located region of the femur.

In Example 18, the system of any one or any combination of Examples 12-17, can further comprise a femoral insert that can be configured to be secured within the box cutout. Together the femoral insert and the femoral component can be configured to form a trial femoral prosthesis.

In Example 19, a method of preparing a distal femur for a posterior stabilized prosthetic knee assembly, the method can comprise positioning a femoral component to engage a resected distal surface of a femur, the femoral component can have a box cutout configured to provide access to a distal centrally located region of the femur, the box cutout can be disposed between a medial condyle, a lateral condyle and an anterior portion of the femoral component, attaching a guide to the femoral component at one or more locations, the guide can comprise a frame forming one or more reference surfaces and an enclosed opening that can be configured to provide access to the box cutout and the distal centrally located region of the femur, inserting a first cutting tool through the opening of the guide, the first cutting tool can have a first portion configured to access the box cutout and the distal centrally located region of the femur, the first cutting tool can have a second portion more proximally disposed than the first portion and having a larger diameter than the first portion that can be configured to contact the guide, and actuating the first cutting tool to cut tissue at the distal centrally located region of the femur.

In Example 20, the method of Example 19, wherein the first cutting tool can comprise a reamer and the reamer can comprise the only cutting tool used to prepare the distal femur for the posterior stabilized prosthetic knee assembly according to the method of Example 19.

In Example 21, the method of any one or any combination of Examples 19-20, further comprising guiding the first cutting tool along the one or more reference surfaces to remove the tissue from the distal centrally located region of the femur.

In Example 22, the method of any one or any combination of Examples 19 and 21, can further comprise inserting a second cutting tool through a different portion of the opening of the guide than the first cutting tool after actuation of the first cutting tool is completed and the first cutting tool is removed from the guide, the second cutting tool can have a first portion configured to access the box cutout and the distal centrally located region of the femur, the second cutting tool can have a second portion more proximally disposed than the first portion having a larger diameter than the first portion that can be configured to contact the guide, and actuating the second cutting tool to cut the tissue of the distal centrally located region of the femur.

In Example 23, the method of Example 22, wherein actuating can include plunging one or more of the first cutting tool and the second cutting tool into the tissue.

In Example 24, the apparatuses, systems or methods of any one or any combination of Examples 1-23 can optionally be configured such that all elements or options recited are available to use or select from.

These and other examples and features of the present apparatuses and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to devices, systems and methods that can be used in knee procedures including a total knee replacement procedure (TKA) that is posterior stabilized. More particularly, the present application relates to femoral components that define box cutouts, to cutting tools that can access a distal centrally located region of the femur through the box cutouts to remove and/or break apart tissue therein, and to guides that are mountable to the femoral component and that can guide cutting performed by the cutting tools and can set an access depth for the cutting tools.

As used herein, the terms "proximal" and "distal" should be given their generally understood anatomical interpretation. The term "proximal" refers to a direction generally toward the torso of a patient, and "distal" refers to the opposite direction of proximal, i.e., away from the torso of a patient. It should be understood that the use of the terms "proximal" and "distal" should be interpreted as though the patient were standing with the knee joint in extension despite the apparatuses described herein generally being used with the knee joint in flexion. The intent is to differentiate the terms "proximal" and "distal" from the terms "anterior" and "posterior". As used herein, the terms "anterior" and "posterior" should be given their generally understood anatomical interpretation. Thus, "posterior" refers to a rear of the patient, e.g., a back of the knee. Similarly, "anterior" refers to a front of the patient, e.g., a front of the knee. Thus, "posterior" refers to the opposite direction of "anterior".

Figure 1:
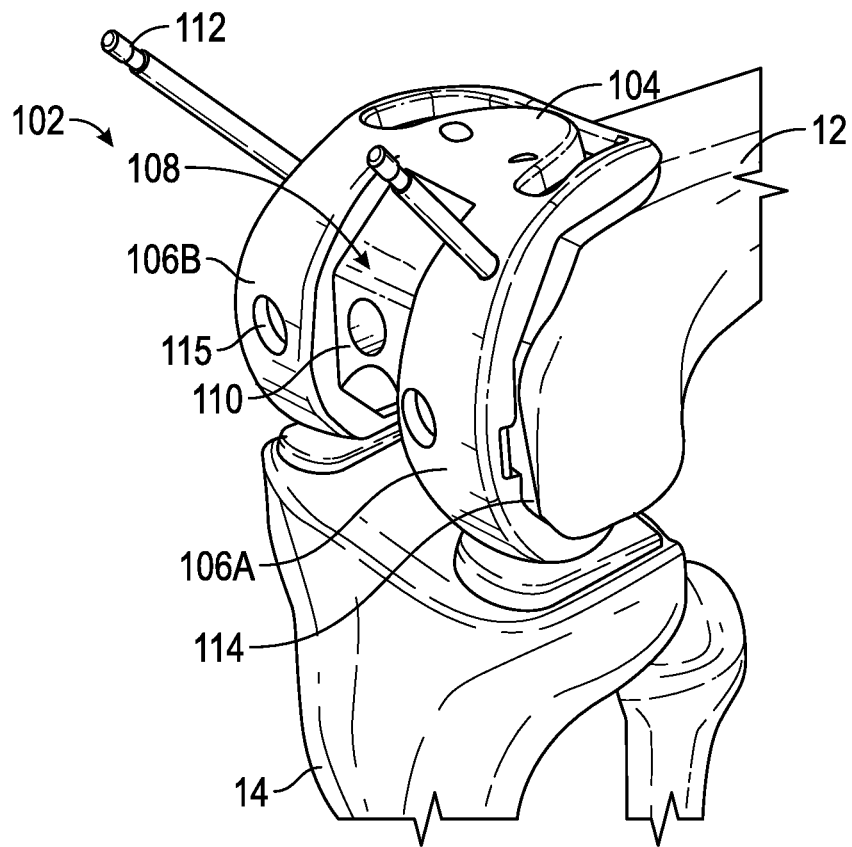
FIG. 1 is a perspective view of a knee joint with a femoral component mounted to a femur, the femoral component can have a box cutout exposing a distal centrally located region of the femur according to an example of the present application.

FIG. 1 shows a perspective view of the patient's distal femur 12 and proximal tibia 14 along with a femoral component 102 mounted to the distal femur 12. FIG. 1 illustrates the knee prior to implantation of a tibial component and prior to further bone resections to the distal femur 12 that will be discussed subsequently.

In the example of FIG. 1, the femoral component 102 can include an anterior portion 104, a lateral condyle 106A, a medial condyle 106B, and a box cutout 108. The distal femur 12 can have a distal centrally located region 110 that is accessible via the box cutout 108.

Fasteners 112 (such as bone screws, nails, or pins) can be used to affix the femoral component 102 to the distal femur 12. The femoral component 102 can be configured to engage a resected distal surface 114 of the femur 12 along an interior surface. An opposing surface from the interior surface can act as an articular surface (e.g., along the lateral condyle 106A and the medial condyle 106B) for the femoral component 102. The box cutout 108 can comprise an opening that provides access to the distal centrally located region 110 of the femur 12. The box cutout 108 can be disposed between the medial condyle 106B, the lateral condyle 106A and the anterior portion 104 of the femoral component 102. Indeed, according to some examples, surfaces of the medial condyle 106B, the lateral condyle 106A and the anterior portion 104 can define the box cutout 108. The femoral component 102 can include fixation apertures 115 that can be used for connection with a guide as will be illustrated subsequently.

Figure 2:
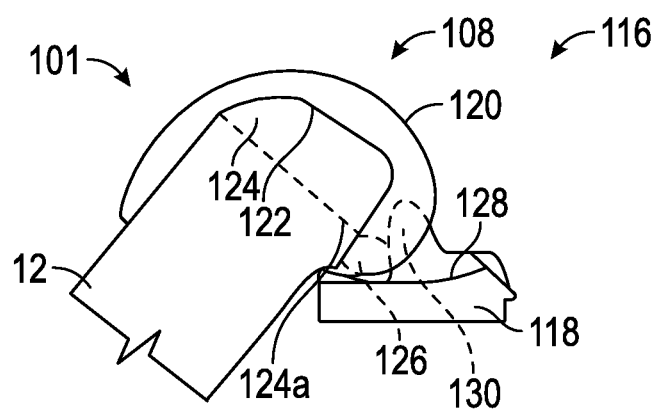
FIG. 2 shows an assembly of the femoral component of FIG. 1 with a tibial component according to an example of the present application.

FIG. 2 illustrates a posterior-stabilized knee assembly 116 after the knee joint including the distal femur 12, has been fully prepared. Examples of such preparation techniques will be discussed subsequently with reference to FIGS. 3 to 5. The knee assembly 116 can include a permanent femoral implant 101 and a permanent tibial implant 118, which can be configured to attach to a patient's proximal tibia (tibia 14 in FIG. 1).

The femoral implant 101 of the knee assembly 116 can include an articulating surface 120 that articulates against the tibial implant 118, as shown in FIG. 2, and an opposing bone-contacting surface 122 that rests against the patient's distal surface 114 of the femur 12.

In FIG. 2, the distal centrally located region 110 of the femur 12 has been removed to create a recess 124. The recess 124 can sometimes be referred to a box or cavity. The box cutout 108 can define an opening for the recess 124. As shown in FIG. 2, a surface 124a (indicated in dashed) of the femur 12 defining an inner most portion of the recess 124 can be disposed inward of the resected distal surface 114. The recess 124 can extend medial-lateral and anterior-posterior as well as proximal-distal and can have a medial-lateral distance similar to that of the box cutout 108.

As shown in the example of FIG. 2, a cam 126 can be added to the femoral implant 101. The tibial implant 118 can include an articulating surface 128 that can be configured to articulate against the femoral implant 101. The tibial implant 118 also include a spine 130 that can extend proximally from the articulating surface 128.

When the patient's knee joint is extended, the spine 130 can be received freely within the box cutout 108 and the recess 124. However, when the patient's knee joint is moved to a flexion position, such as shown in FIG. 2, the spine 130 can abut the cam 126 to resist posterior translation of the tibial implant 118 relative to the femoral implant 101.

Figure 3:
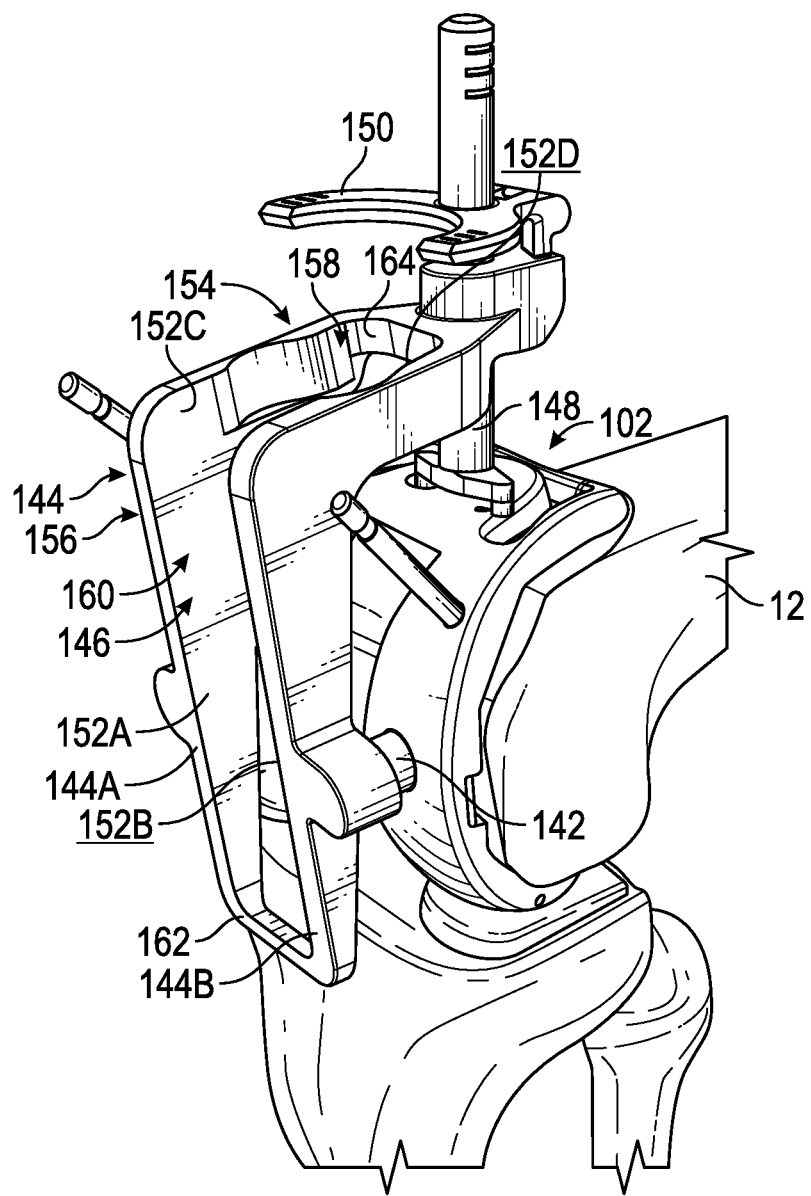
FIG. 3 is a perspective view of a guide mounted to the femoral component of FIG. 1 according to an example of the present application.
Figure 4:
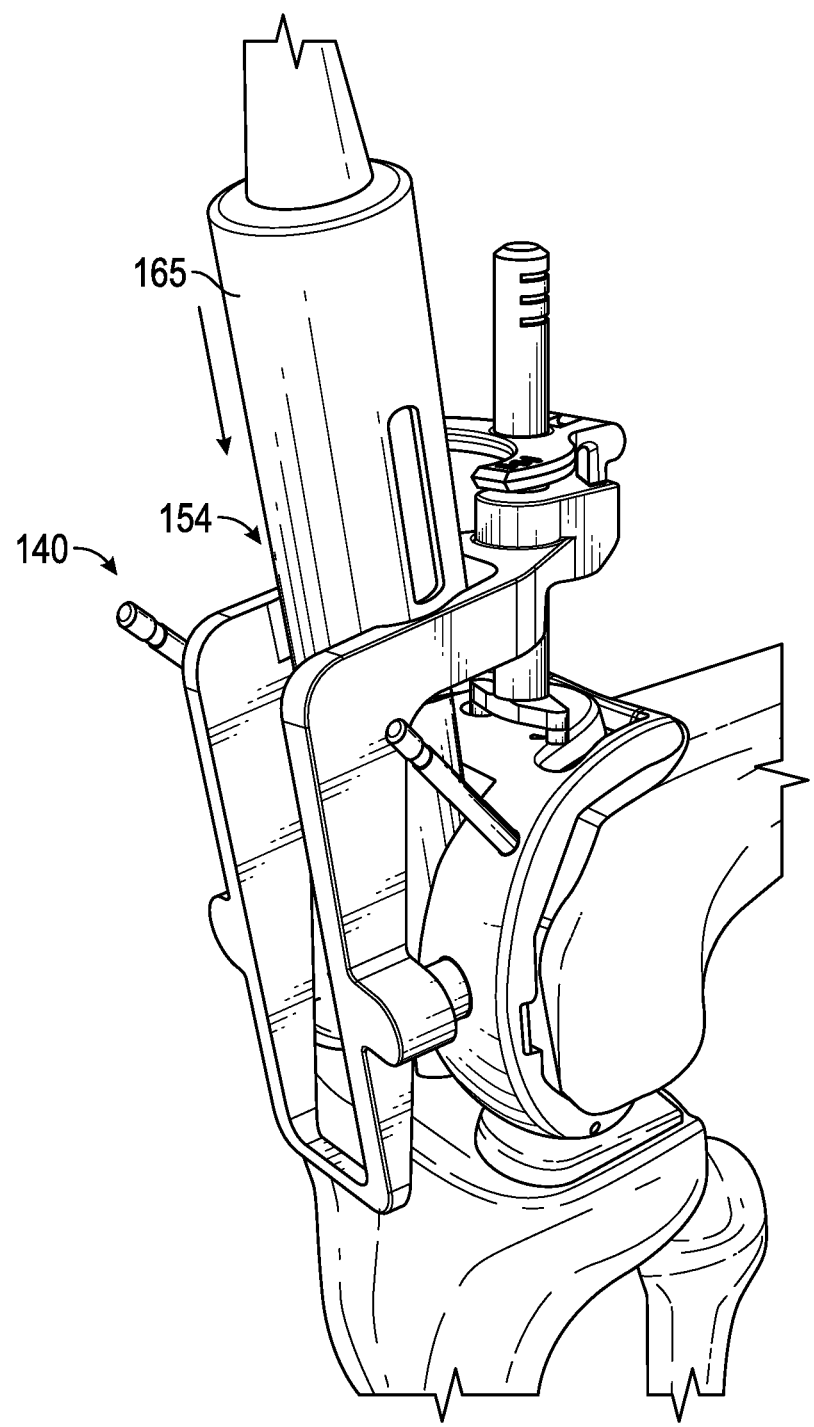
FIG. 4 is a perspective view of the guide and the femoral component of FIG. 3 interacting with a first cutting tool according to an example of the present application.
Figure 5:
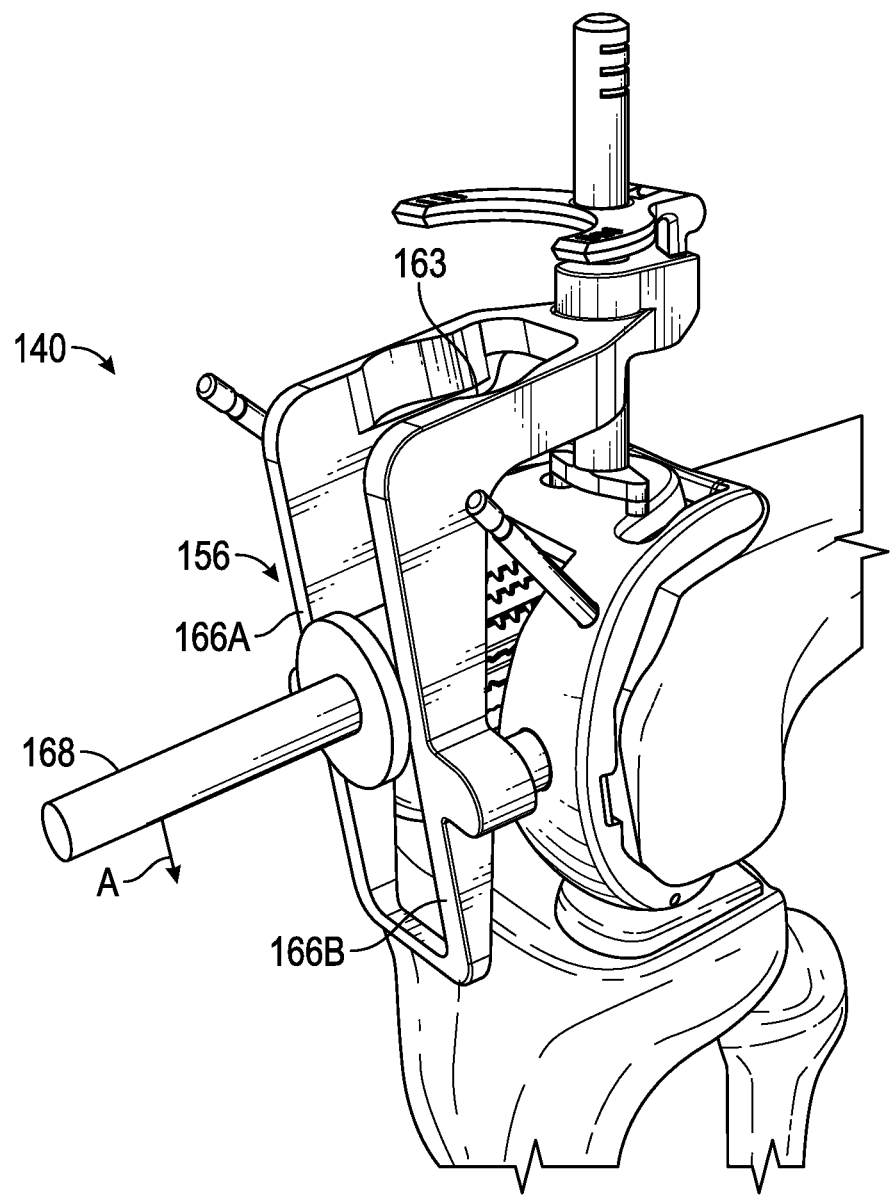
FIG. 5 is a perspective view of the guide and the femoral component of FIG. 3 interacting with a second cutting tool according to an example of the present application.

Referring to FIG. 3, a perspective view of the knee from FIG. 1 is illustrated with addition of a guide 140 with the trial femoral implant 102 (previously illustrated in FIG. 1). FIGS. 3 to 5 provide an example of preparing the patient's distal femur with a recess (e.g., recess 124 of FIG. 2) such as for the posterior stabilized knee assembly 116 (FIG. 2). The guide 140 can include fixation elements 142, a frame 144, an opening 146, a lock coupling 148, and a locking mechanism 150. The frame 144 can include guide surfaces 152A, 152B, 152C, and 152D, a first frame portion 154, and a second frame portion 156. The opening 146 can include a first opening portion 158 and a second opening portion 160.

The guide 140 can be configured to selectively connect to a trial femoral component 102 at one or more locations with the fixation elements 142 and the lock coupling 148 via the locking mechanism 150. In the example of FIGS. 3 to 5, the guide 140 can be spaced from the femur 12 and can connect only with the femoral component 102 for assembly and mounting. The guide 140 can comprise an open frame construction. The frame 144 can define the opening 146 and can include two spaced apart legs 144A and 144B, which can be connected together at an anterior distal end 162 and a posterior proximal end 164. The legs 144A and 144B can have the guide surfaces 152A, 152B, 152C, and 152D as the interior surfaces thereof.

The frame 144 can couple with the lock coupling 148 adjacent the first opening portion 158. The lock coupling 148 can be configured to connect to the femoral component 102 and can extend outwards therefrom to space the frame 144 from the femoral component 102. According to the example of FIGS. 3 to 5, the lock coupling 148 can connect with the locking mechanism 150 outward of and generally proximally above the frame 144.

The guide surfaces 152A, 152B, 152C, and 152D can comprise the interior generally interfacing surfaces of the frame 144. Thus, the guide surfaces 152A, 152B, 152C, and 152D can define the opening 146. The one or more surfaces 152A, 152B, 152C, and 152D can comprise a first guide surface (e.g., 152A, 152C) spaced by the opening 146 from a second guide surface (e.g., 152B, 152D). A medial-lateral distance between and positioning of the first (e.g., 152A, 152C) and the second guide surfaces (e.g., 152B, 152D) can correspond generally to a medial-lateral distance and positioning of surfaces of the lateral and the medial condyles 106A, 106B (FIG. 1) that form the box cutout 108 (FIG. 1). According to some examples, the proximal-distal extent of the first and second surfaces (e.g., 152A and 152B) can exceed a proximal-distal extent defined by the box cutout 108. This arrangement can allow for tracking of a cutting tool along the guide 140 and insertion of the tool at multiple angles as desired.

The first frame portion 154 can be disposed to the posterior of the second frame portion 156 and can define the first opening portion 158. The first frame portion 154 can extend and can be oriented generally anterior-posterior. Thus, the first opening portion 158 can have a generally anterior-posterior orientation. The second frame portion 156 can define the second opening portion 160. The second frame portion 156 can extend and can be oriented generally proximal-distal. Thus, the second opening portion 160 can have a generally proximal-distal orientation.

The opening 146 through the frame 144 can be configured to provide access to the box cutout 108 (FIG. 1) and the distal centrally located region 110 (FIG. 1) of the femur 12 for tools that can be used for removal of bone and/or soft tissue in the distal centrally located region 110 to form the recess 124 (FIG. 2). More particularly, the configuration of the frame 144 (having both generally anterior-posterior extending legs as well as generally proximal-distal extending legs) can allow for access to the box cutout 108 (FIG. 1) and the distal centrally located region 110 (FIG. 1) for cutting tools from various orientations including a generally proximal-distal orientation and a generally anterior-posterior orientation as is illustrated in FIGS. 4 and 5.

FIGS. 4 and 5 show the first frame portion 154 of the guide 140 can include a recessed lip 163 (FIGS. 5, 10 and 10A) configured to be engaged by a portion of a first cutting tool 165 (e.g., a trephine). The first cutting tool 165 can be configured to cut tissue in the distal centrally located region 110 (FIG. 1). Such cutting can be done in a generally proximal-distal direction according to the example of FIG. 4.

In FIG. 5, the second frame portion 156 of the guide 140 can include at least one anterior surface 166A, 166B configured to act as a stop to set a desired access depth for a second cutting tool 168 (e.g., a reamer). The one or more guide surfaces 152A, 152B, 152C, and 152D (FIG. 3) can be configured to act as a track to be traced along by the second cutting tool 168 (as indicated by arrow A) in removing bone and/or tissue from the distal centrally located region 110 (FIG. 1) of the femur 12. The track of the second cutting tool 168 can be generally oriented in the proximal-distal direction (although some change in anterior-posterior position can occur with proximal-distal travel) as defined by the anterior surfaces 166A, 166B in FIG. 5. According to some examples, only the second cutting tool 168 may be used in removal and cutting of tissue from the distal centrally located region 110, and the first cutting tool 165 may not need to be used.

As shown in FIGS. 4 and 5, the cutting tool(s) (e.g., the first cutting tool 165 and/or the second cutting tool 168) can include a first section that can be configured (e.g., having a proximal-distal length and a diameter sufficiently small) to access the box cutout 108 (FIG. 1) and the distal centrally located region 110 via the opening 146. The cutting tool(s) can have a second section more proximally disposed than the first portion having a larger diameter than the first section configured to contact the guide 140.

The guide 140 and cutting tool(s) (e.g., the first cutting tool 165 and/or the second cutting tool 168) can be configured such that insertion of the cutting tool(s) into the guide 140 occurs until contact between the second section of the cutting tool(s) and the guide. Such contact can set a desired access depth for the first section of the cutting tool(s) relative to the guide. The desired access depth can allow for removal of a desired amount of the bone and/or soft tissue in the distal centrally located region 110.

Figure 6:
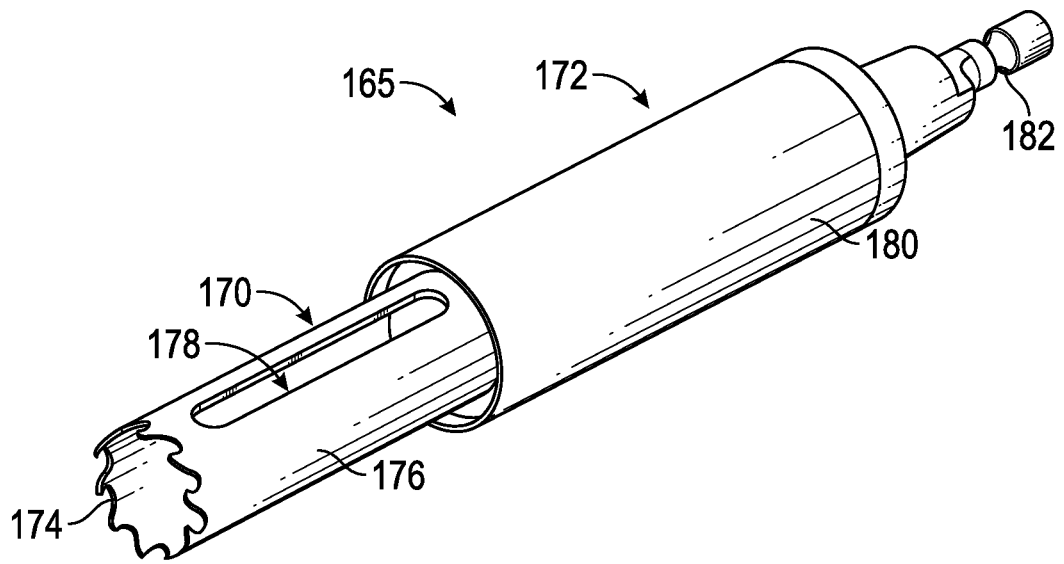
FIG. 6 is a perspective view of the first cutting tool according to example of the present application.
Figure 7:
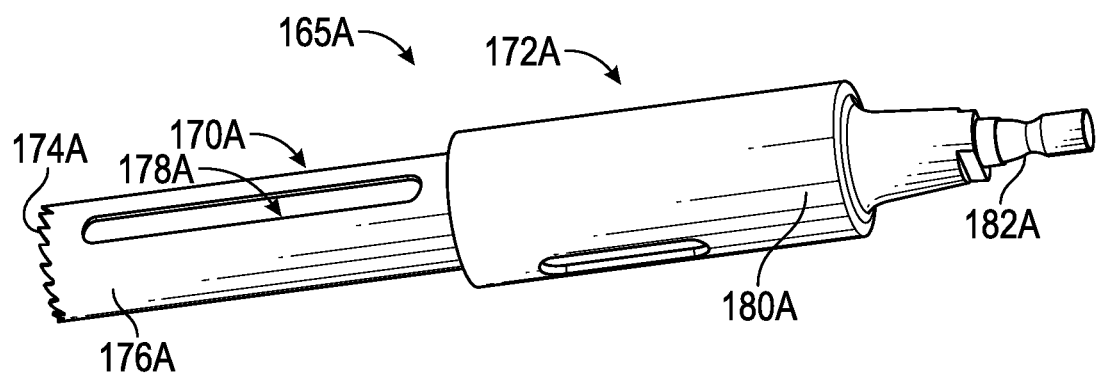
FIGS. 7 and 7A are perspective views of another example of the first cutting tool.
Figure 7A:
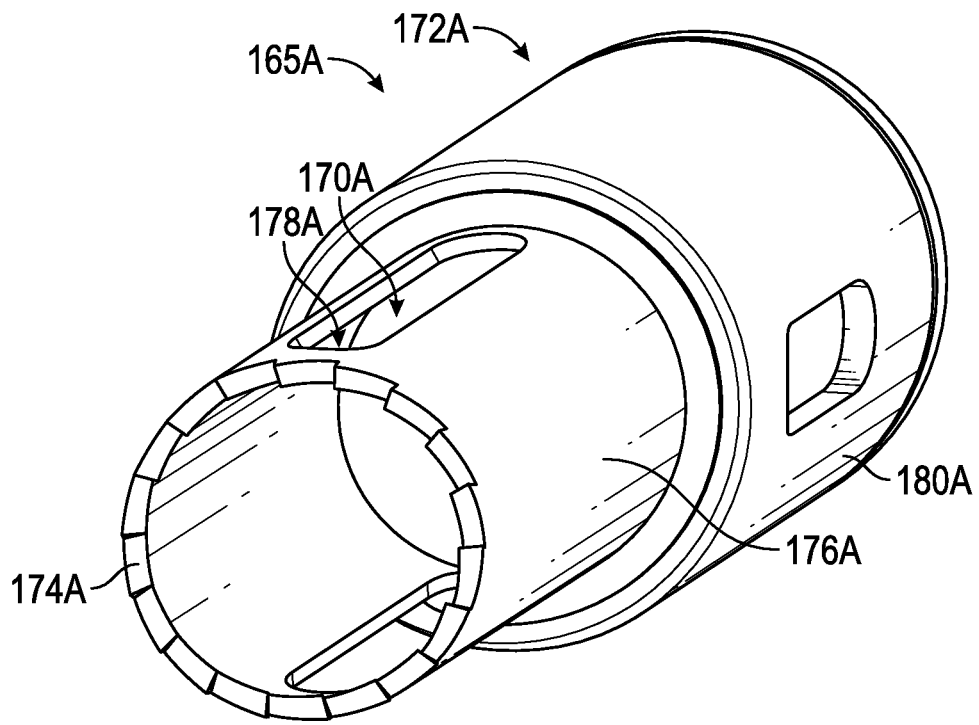

FIGS. 6, 7, and 7A show examples of the first cutting tool 165 (FIG. 6) and 165A (FIGS. 7, 7A), comprising the trephine. The first cutting tool 165, 165A can have a first portion such as a distal section 170, 170A and a second portion such as a proximal section 172, 172A. The distal section 170, 170A can have a cutting tip 174, 174A, an open body shaft 176, 176A and slots 178, 178A. The proximal section 172, 172A can include a shaft 180, 180A and a driving head 182, 182A.

The first cutting tool 165, 165A can be used to cut and break apart tissue in a manner know in the art. According to some examples, actuating the first cutting tool can include plunging the first cutting tool 165, 165A into the soft tissue (with and/or without) and then rotating the first cutting tool 165, 165A. The distal section 170, 170A can be coupled to the proximal section 172, 172A. The cutting tip 174, 174A can be disposed on distal most rim portion of the open body shaft 176, 176A. The slots 178, 178A can be defined by the open body shaft 176, 176A and can be disposed proximal of the cutting tip 174, 174A. The slots 178, 178A can extend generally proximally-distally and can be spaced apart circumferentially across the open body shaft 176, 176A from one another. The slots 178, 178A can communicate with an inner cavity of the first cutting tool 165, 165A. The open body shaft 176, 176A can be configured to define the inner cavity (see FIG. 7A) having an opening at a distal end thereof. The shaft 180, 180A can be located proximal of and can be disposed around portions of the open body shaft 176, 176A. The shaft 180, 180A can couple with the driving head 182, 182A that can be configured to couple with an actuating device.

As shown in FIGS. 4 and 6-7A, the distal section 170, 170A can be configured (e.g., having a proximal-distal length and a diameter sufficiently small) to access the box cutout 108 (FIG. 1) and the distal centrally located region 110 via the opening 146. The proximal section 172, 172A can have a larger diameter than the distal section 170, 170A can be configured to contact the guide 140.

Figure 8:
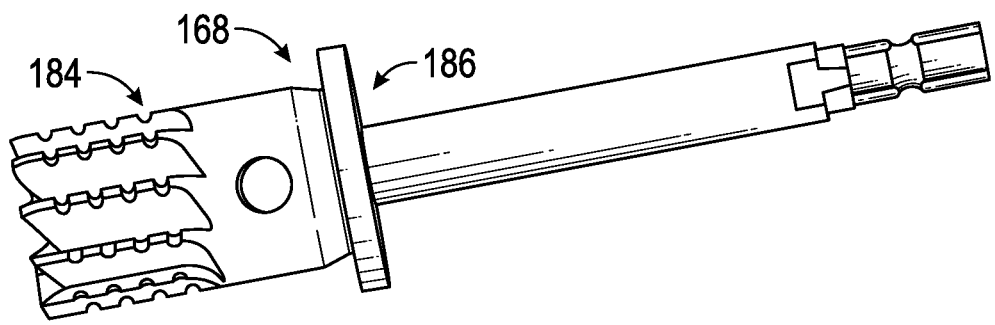
FIGS. 8, 9A and 9B are perspective views of the second cutting tool according to two different examples of the present application.

FIG. 8 shows an example of the second cutting tool 168 comprising the reamer. The second cutting tool 168 can have a first portion such as a distal section 184 and a second portion such as a proximal section 186.

Figure 11:
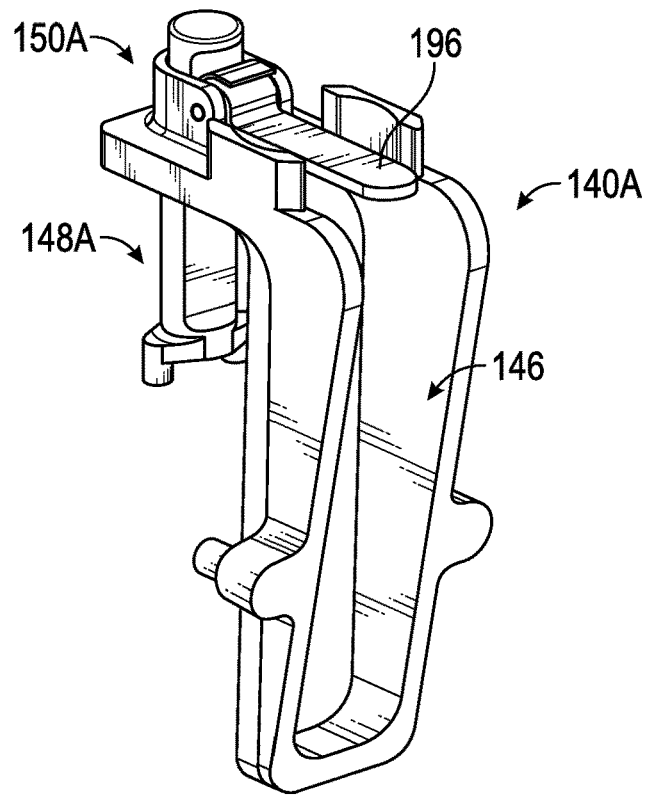
FIG. 11 is a perspective view of a guide, the locking mechanism, and a coupling according to another example of the present application.
Figure 11A:
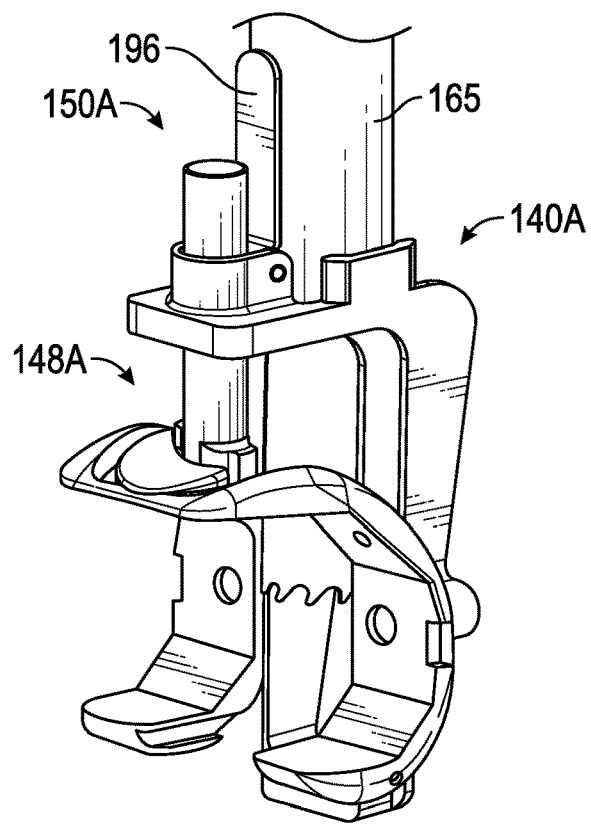
FIG. 11A is a perspective view of the guide and the secondary guide of FIG. 11 and a femoral component interacting with the first cutting tool according to an example of the present application.
Figure 11B:
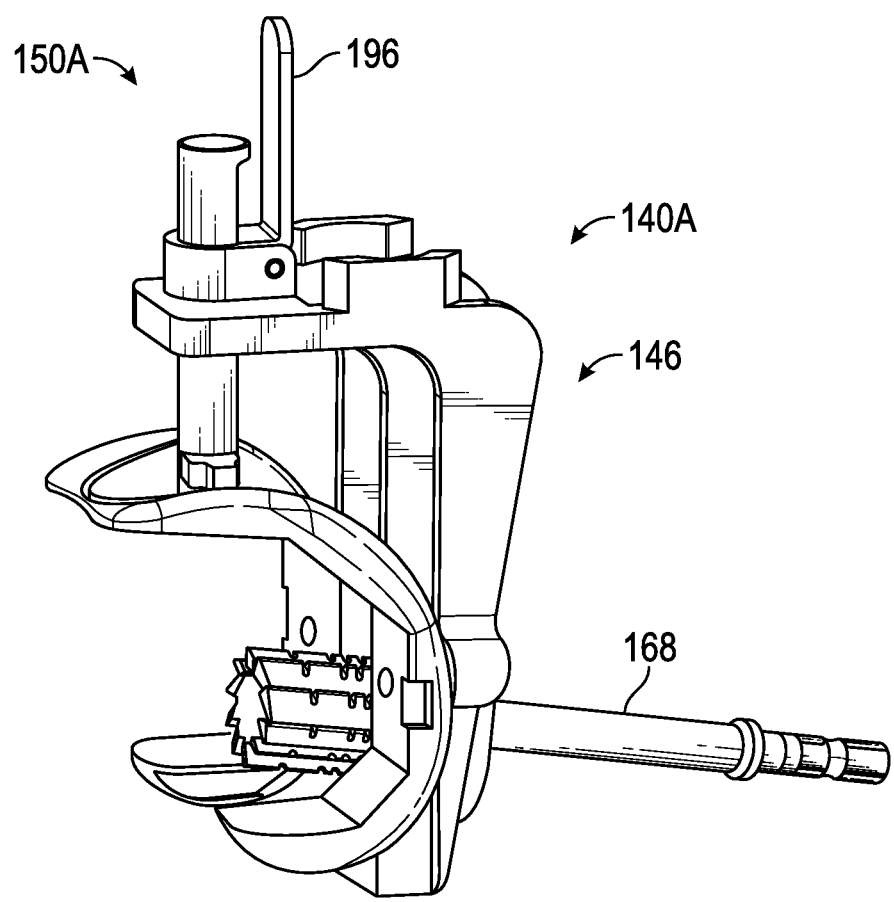
FIG. 11B is a perspective view of the guide and the locking mechanism of FIG. 11 and the femoral component of FIG. 11A interacting with the second cutting tool according to an example of the present application.

As shown in FIGS. 5, 8, and 11B, the distal section 184 can be configured (e.g., having a proximal-distal length and a diameter sufficiently small) to access the box cutout 108 (FIG. 1) and the distal centrally located region 110 via the opening 146. The proximal section 186 (more proximally disposed than the distal section 170) can have a larger diameter than the distal section 184 can be configured to contact the guide 140.

Figure 9A:
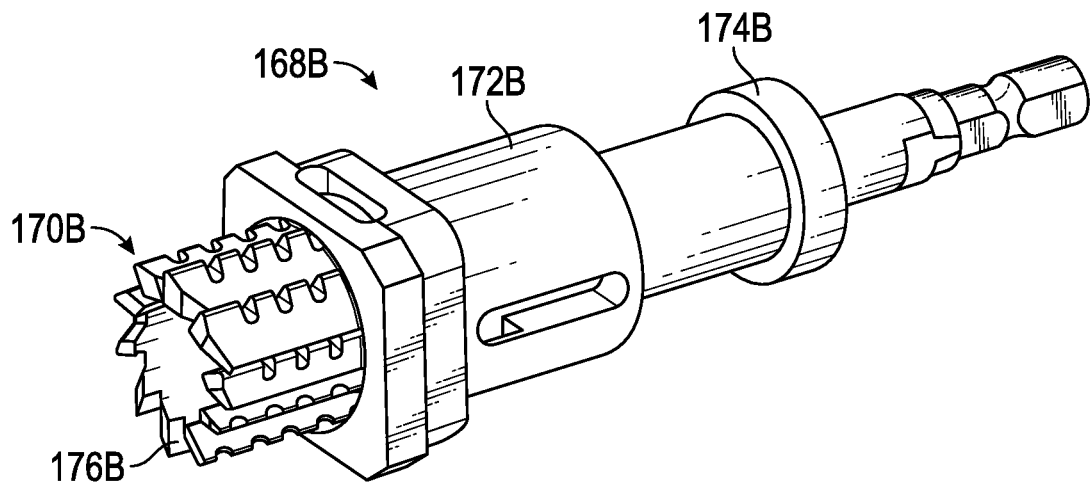
Figure 9B:
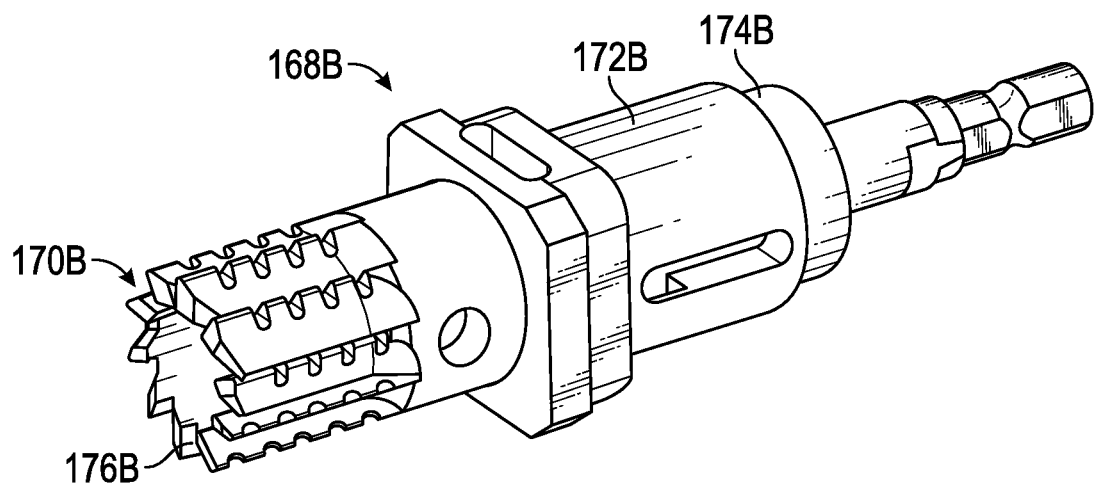

FIGS. 9A and 9B show another example of the second cutting tool 168B comprising a guided reamer 170B and bushing 172B. The bushing 172B can act as a guide for the reamer 170B and can be disposed about the reamer 170B. The reamer 170B can be movable axially relative to the bushing 172B as illustrated in FIGS. 9A and 9B. More particularly, FIG. 9A shows the reamer 170B retracted within the bushing 172B. FIG. 9B shows the reamer 170B extended to a second position relative to the bushing 172B. This second position can be a position used when performing a mill cut. Similar to the embodiment of FIG. 8, the second cutting tool 168A can include a depth stop 174B proximal to a cutting end 176B.

According to one example, the guide bushing 172B can decouple rotation of the reamer 170B rotation from the guide. This can allow for a smoother transition of the reamer 170B in distal-proximal direction (while knee is in flexion). The bushing 172B can linearly guide the reamer 170B during a plunging operation in a smooth, linear manner. This can allow the cutting flutes/blades to avoid contact with the guide. Thus, the configuration disclosed can increase a usable life of the instruments. According to some examples, actuating the second cutting tool 168, 168B can include plunging the second cutting tool 168, 168B into the soft tissue (with and/or without) and then rotating the second cutting tool 168, 168B.

Figure 10:
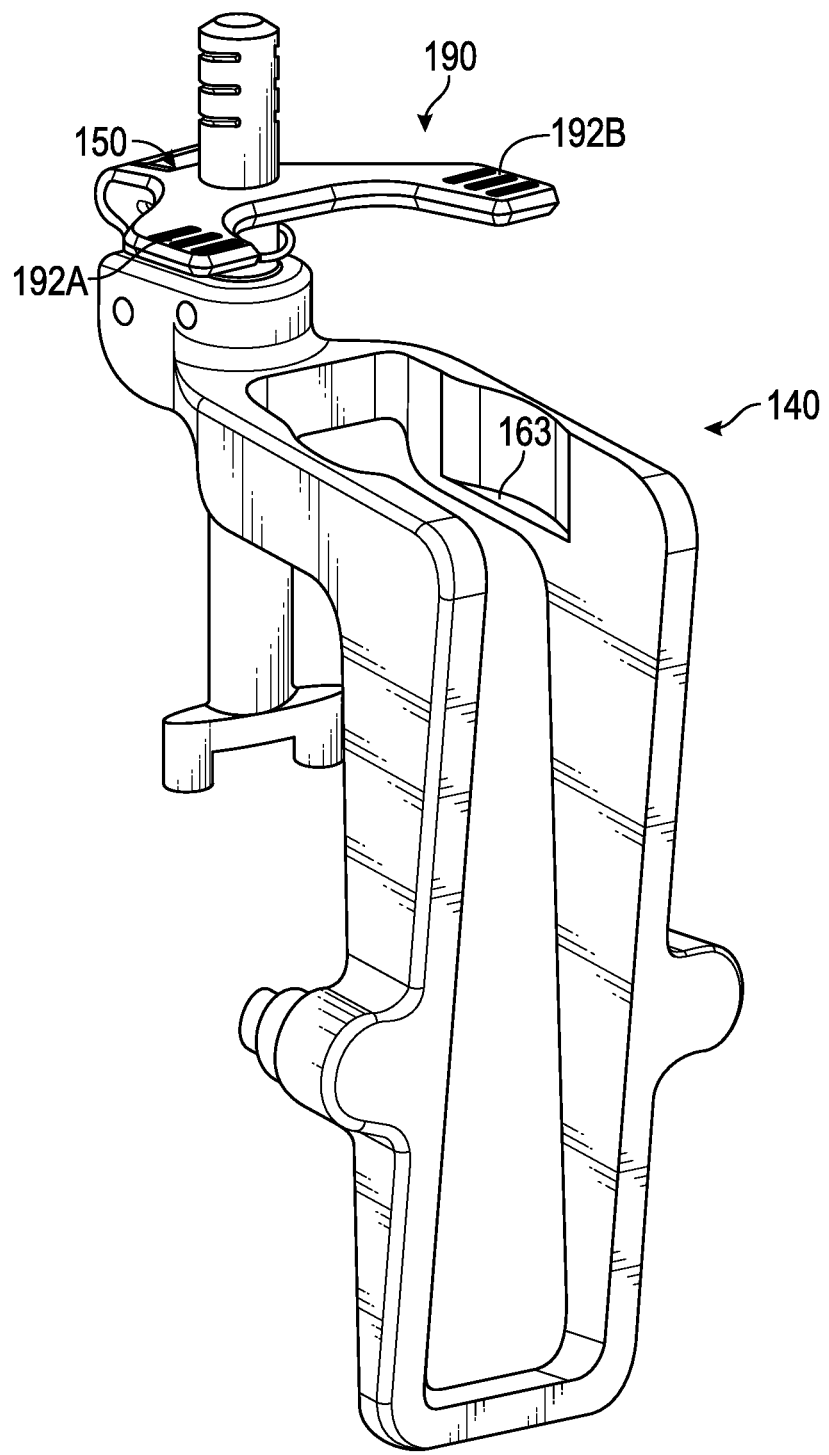
FIG. 10 is a perspective view of the guide, a locking mechanism, and a coupling according to example of the present application.
Figure 10A:
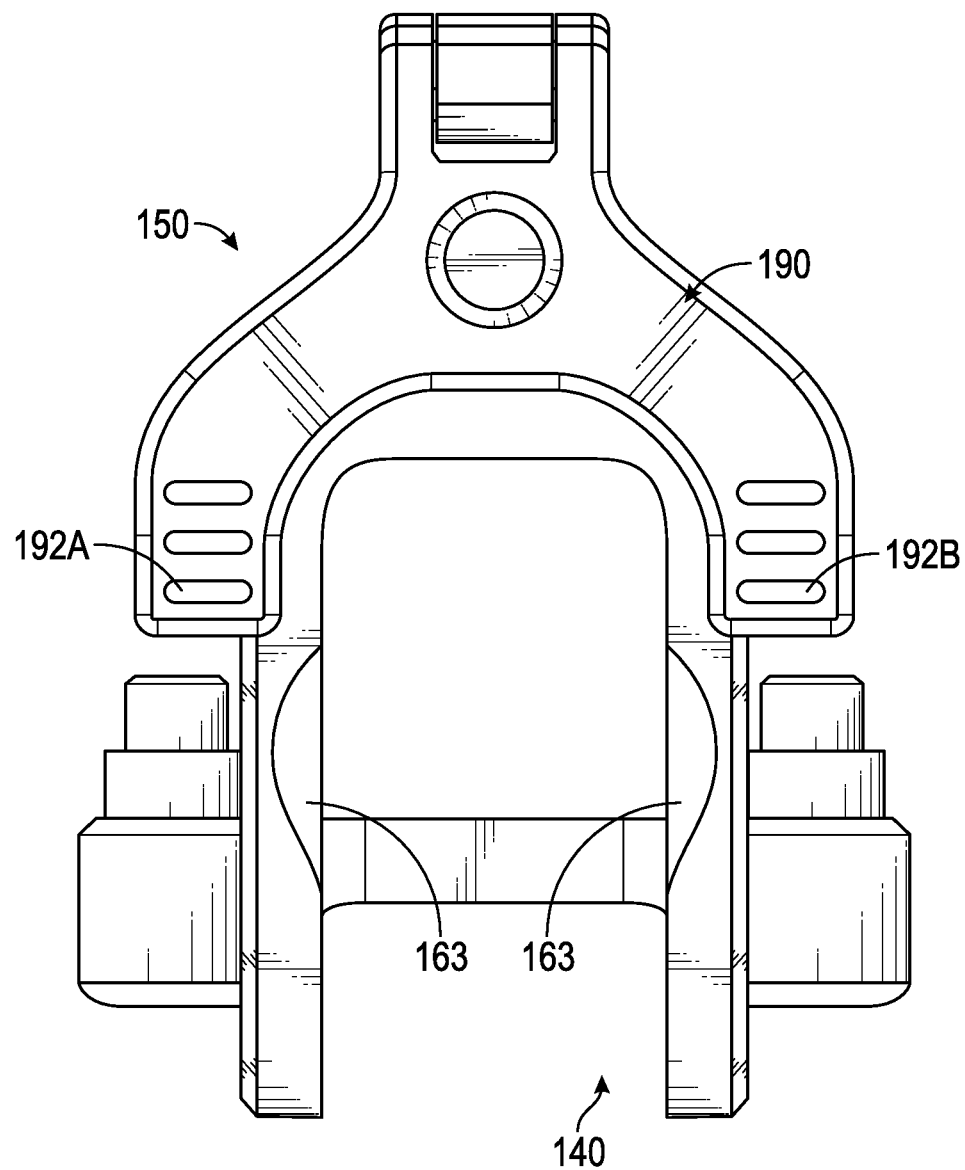
FIG. 10A is a plan view of a proximal portion of the guide and the locking mechanism of FIG. 10.

FIGS. 10 and 10A illustrate the guide 140 in further detail according to one example. The locking mechanism 150 can comprise a locking lever 190 having first and second projections 192A, 192B. As previously discussed, the guide 140 can include the recessed lip 163. The recessed lip 163 can set a desired access depth for the first cutting tool 165, 165A. The locking lever 190 can be configured to provide clearance for the first cutting tool 165, 165A between the first and second projections 192A, 192B.

FIGS. 11, 11A and 11B show another example of a guide 140A and a locking mechanism 150A. FIG. 11B shows the second cutting tool 168 can access the box cutout 108 (FIG. 1) and the distal centrally located region 110 via the opening 146.

In the Example of FIGS. 11 to 11B, the locking mechanism 150A can include a locking cam member 196 that can be pivoted from a generally anterior-posterior disposition of FIG. 11 to the generally proximal-distal disposition of FIG. 11A. This can allow for fixation between the locking cam member 196 and locking coupling 148 which engages into the femoral component to solidify the assembly.

Figure 12:
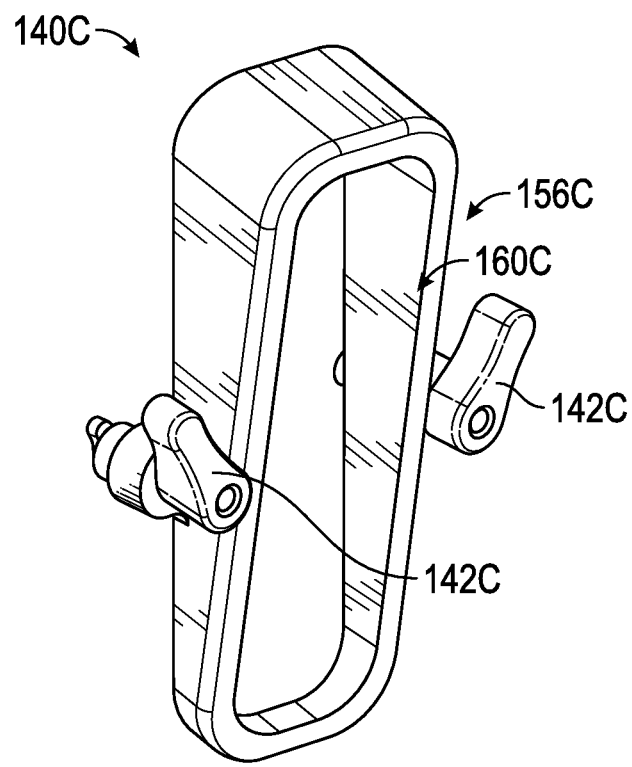
FIG. 12 is a perspective view of a guide with fixation features according to another example of the present application.

FIG. 12 shows another example of a guide 140C that can be utilized with a femoral component 102C (FIGS. 13, 13A and 14) in a manner previously described. The guide 140C may not utilize a coupling as the guides 140, 140B previously illustrated and described. The guide 140C further may or may not include the first opening portion 158 (the generally anterior-posterior opening portion of FIG. 3) previously described and shown. The guide 140C can include a second frame portion 156C that can define the second opening portion 160C (generally proximal-distal opening) as described previously.

Figure 12A:
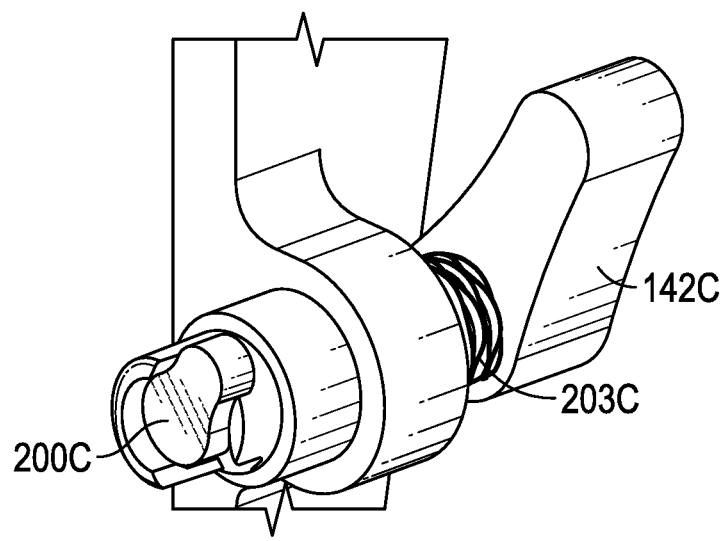
FIG. 12A is an enlarged view of the fixation features of FIG. 12 including locking elements according to an example of the present application.
Figure 13:
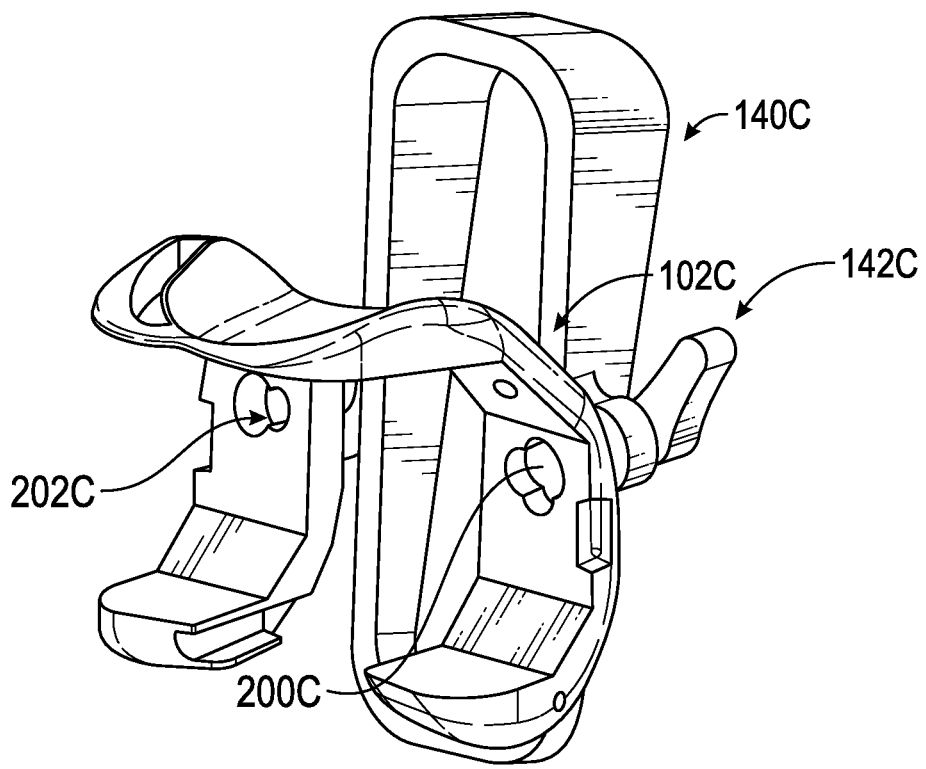
FIGS. 13 and 13A are perspective views of the guide of FIGS. 12 and 12A coupled to a femoral component according to an example of the present application.
Figure 13A:
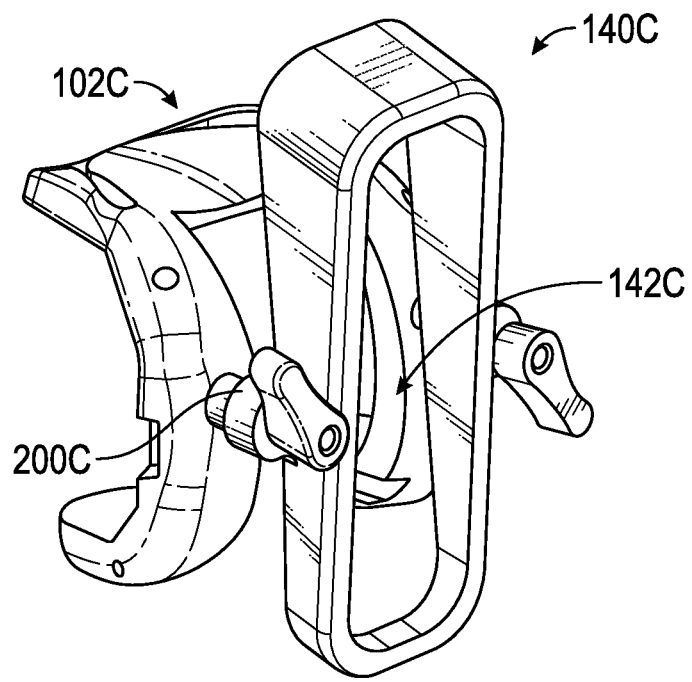
Figure 14:
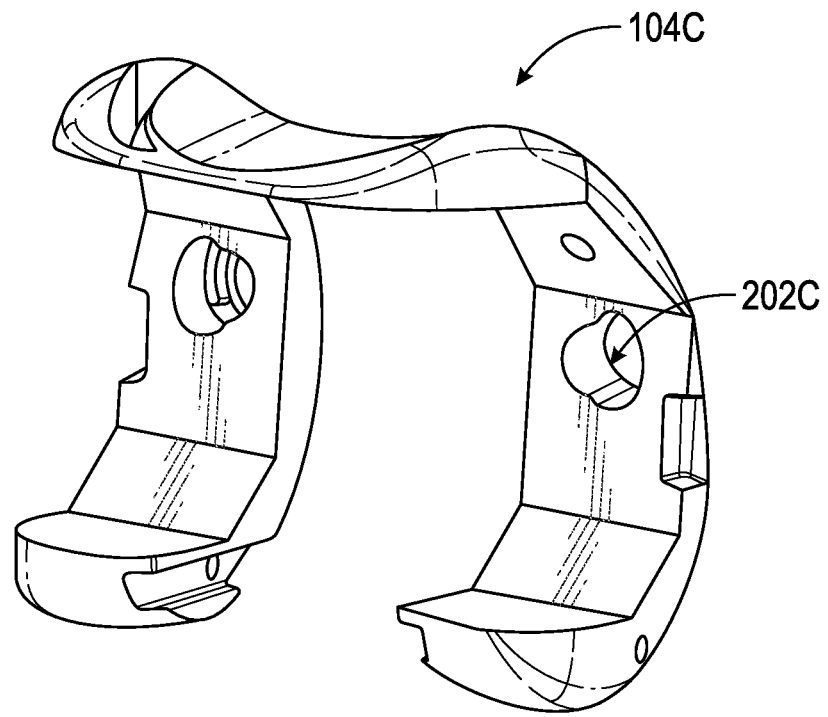
FIG. 14 is a perspective view of the femoral component of FIGS. 13 and 13A.

The guide 140C can include fixation elements 142C that are used to affix the guide 140C to the femoral component 102C as shown in FIGS. 13, and 13A. The fixation elements 142C can comprise a locking feature 200C that is biased into engagement with a mating recess through an aperture 202C in the femoral component 102C as is further illustrated in FIGS. 13A, 14, 14A, 15A and 15B. The bias can be provided by a spring 203C as shown in FIG. 12A.

Figure 14A:
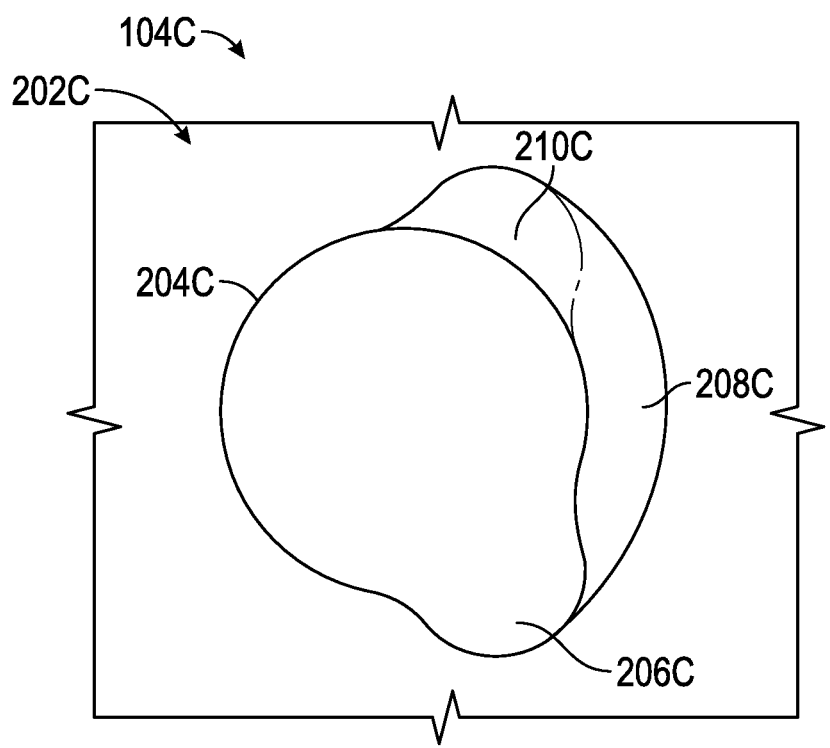
FIG. 14A is an enlarged view of an aperture of the femoral component of FIGS. 13, 13A and 14 according to an example of the present application.
Figure 15A:
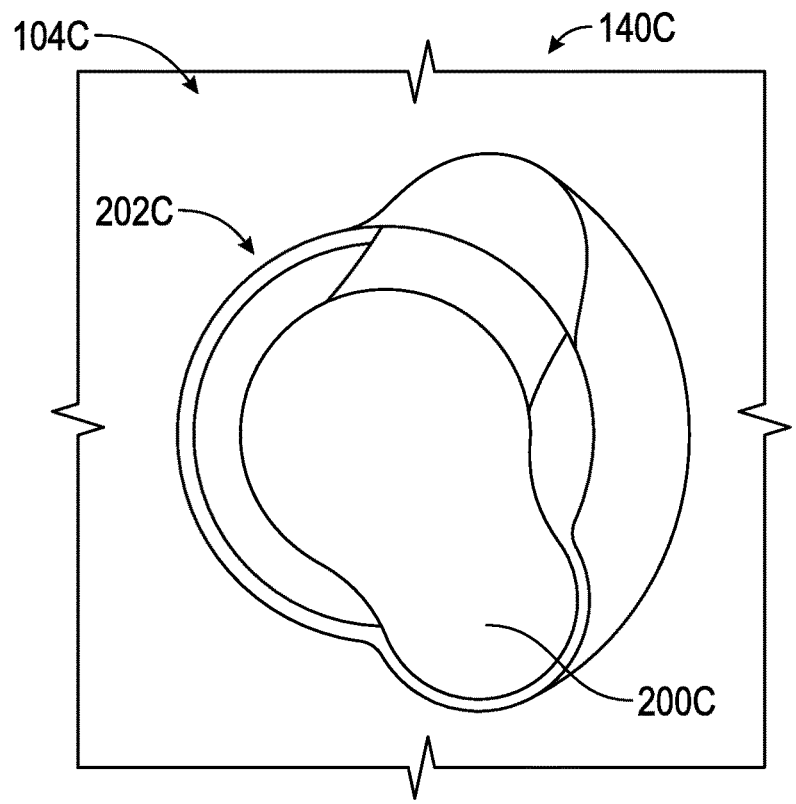
FIGS. 15A and 15B show the locking element of FIGS. 12 and 12A interacting with the aperture of FIGS. 13, 13A, 14 and 14A according to an example of the present application.
Figure 15B:
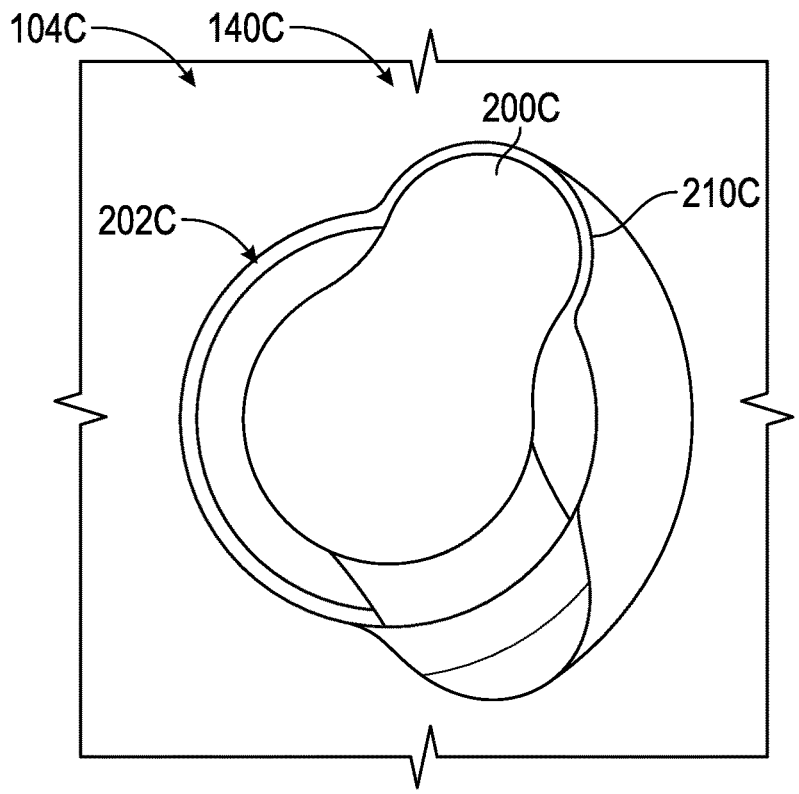

FIGS. 14, 14A, 15A and 15B illustrate the femoral component 102C including the one or more apertures 202C. As shown in FIG. 14A, the aperture 202C can have a semi-circular through bore portion 204C, an element accommodating portion 206C, and a recessed lip 208C. The recessed lip 208C can include an element seat 210C. As shown in FIGS. 15A and 15B, the aperture 202C can receive the locking feature 200C. FIG. 15A illustrates the locking feature 200C in an unlocked position, which can allow for decoupling of the guide 140C from the femoral component 102C. FIG. 15B shows the locking feature 200C in a locked position where the locking feature 200C can be seated in the element seat 210C by the bias of the spring 203C (FIG. 12A). This configuration can be used to couple the guide 140C with the femoral component 102C as shown in FIGS. 13 and 13A.

Figure 16:
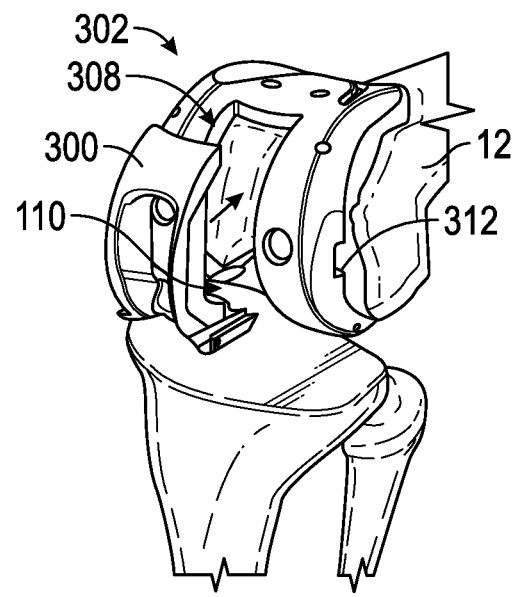
FIG. 16 shows a perspective view of a femoral insert being inserted to couple with a femoral component according to an example of the present application.
Figure 16A:
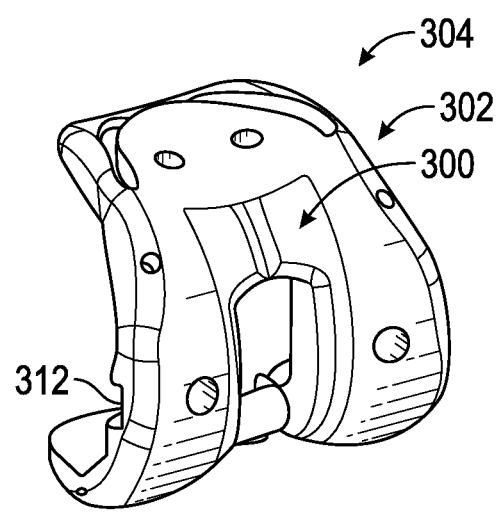
FIG. 16A shows an implant provisional assembly of the femoral insert of FIG. 16 with the femoral component of FIG. 16 according to an example of the present application.

FIGS. 16 and 16A show a femoral insert 300 that can be configured to be secured within a box cutout 308 of a femoral component 302. Together the femoral insert 300 and the femoral component 302 can form a trial femoral prosthesis 304 as shown in FIG. 16A, which can be used as a trial component with a trial tibial component to determine proper sizing for permanent femoral and tibial prostheses. The securing of the femoral insert 300 to the femoral component 302 can occur after a desired amount of tissue has been removed in the distal centrally located region 110 of the femur 12 as shown in FIG. 16.

Figure 17:
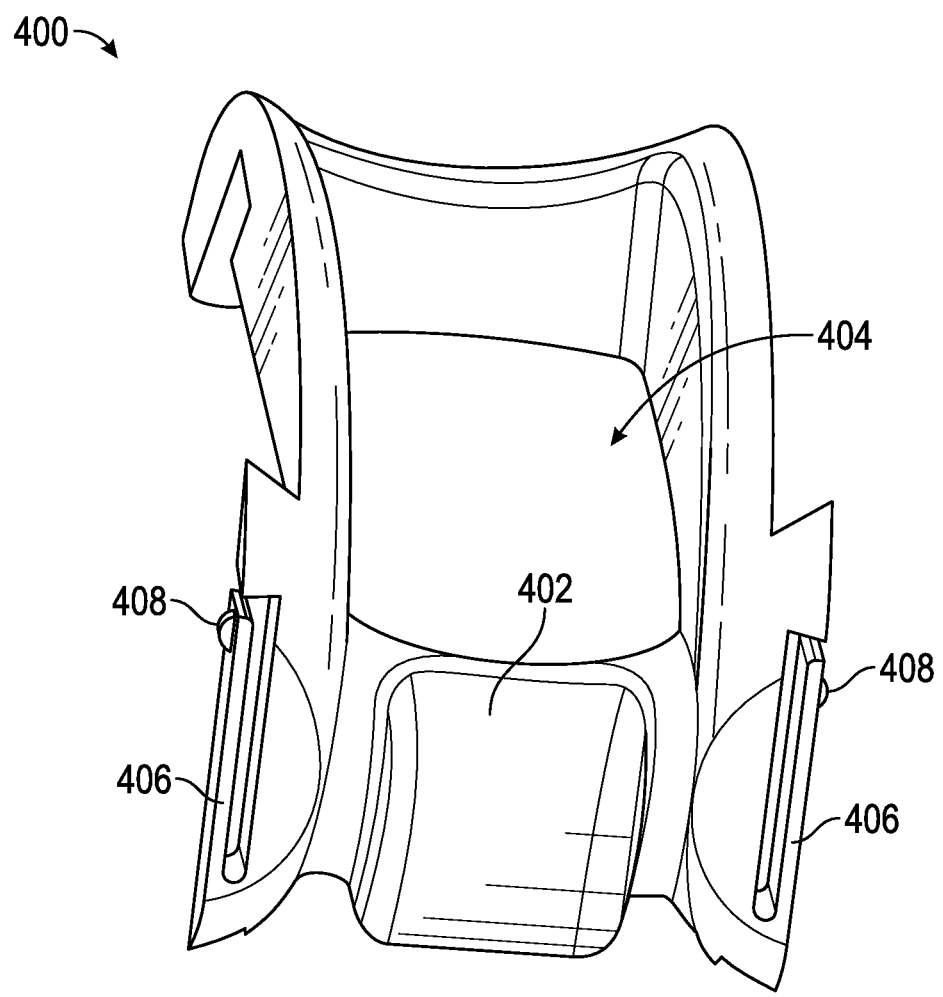
FIG. 17 is a perspective view of the femoral insert showing leaf springs and detents according to an example of the present application.
Figure 18:
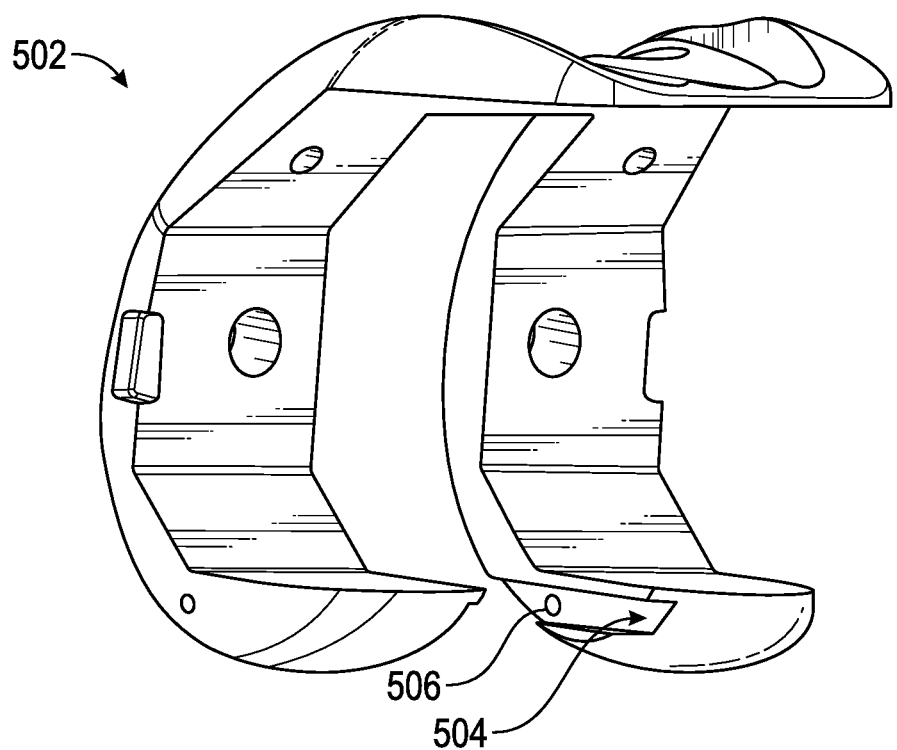
FIGS. 18 and 18A show the femoral component having rails and recesses for receiving the leaf springs and detents according to an example of the present application.

FIG. 17 illustrates a femoral insert 400 according to another example of the present application. FIG. 18 is from a perspective that illustrates the insert 400 can include a cam 402 that defines a portion of an opening 404. The insert 400 can also include leaf springs 406 and detents 408.

Figure 18A:
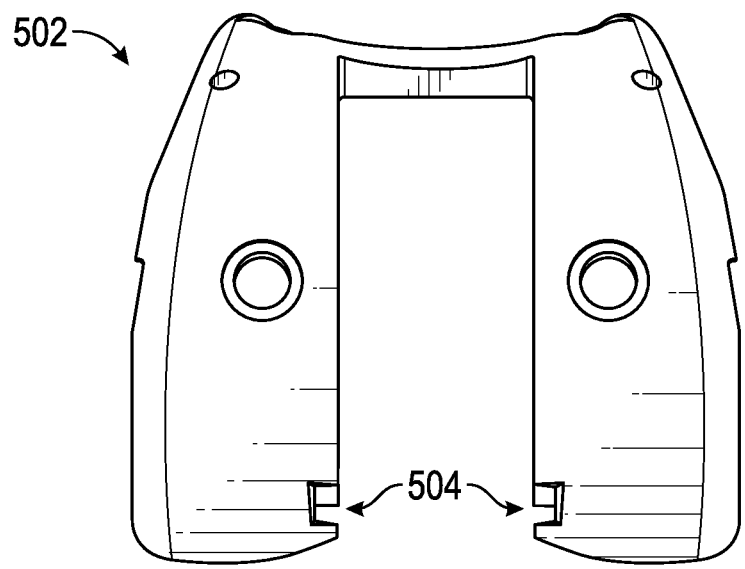

FIGS. 18 and 18A illustrates a femoral component 502 according to an example. The femoral component 502 can include rails 504 and recesses 506 (FIG. 18).

The femoral insert 400 of FIG. 17 can be constructed as an open frame with the cam 402 disposed at a distal portion of the frame. The cam 402 can be configured to interact with a spine of a tibial component as previously discussed with regard to the example of FIG. 2. The frame can define the opening 404, which can be configured to receive the spine allowing the spine to access a recess (e.g., recess 124) in the femur.

The femoral insert 400 can be slid into the femoral component 502 via the generally anterior-posterior extending rails 504. More particularly, the leaf springs 406 and detents 408 can be configured to interact with mating features on the femoral component 502, in particular the rails 504 and recesses 506. The leaf springs 406 can be sized to be received in the rails 504 in an interference arrangement. Similarly, the detents 408 can be received in the recesses 506. Utilization of a leaf spring locking arrangement can eliminate the use of difficult to clean components such as ball plungers.

Figure 19:
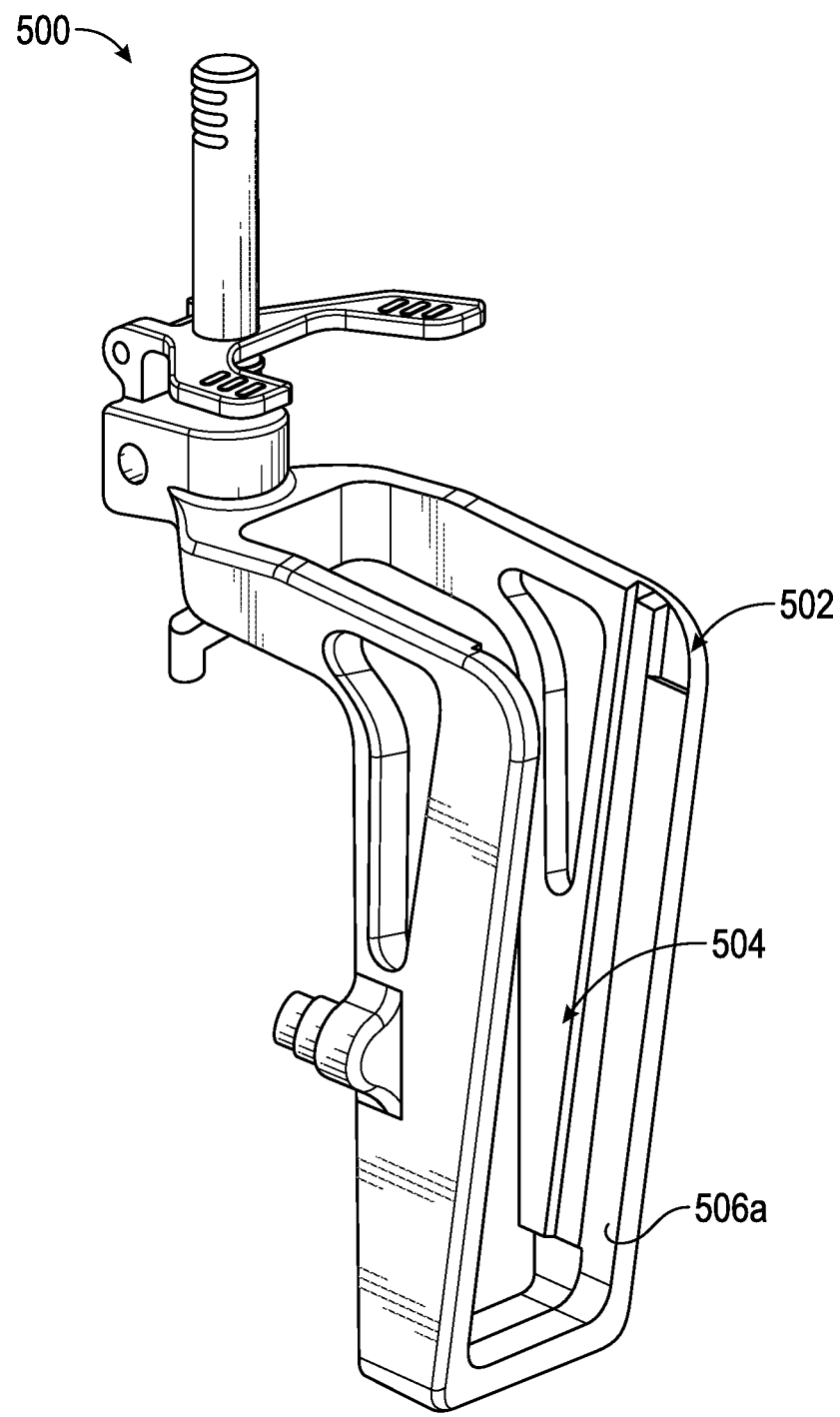
FIGS. 19 and 19A show perspective views of a guide, the locking mechanism, and a coupling according to yet another example of the present application.
Figure 19A:
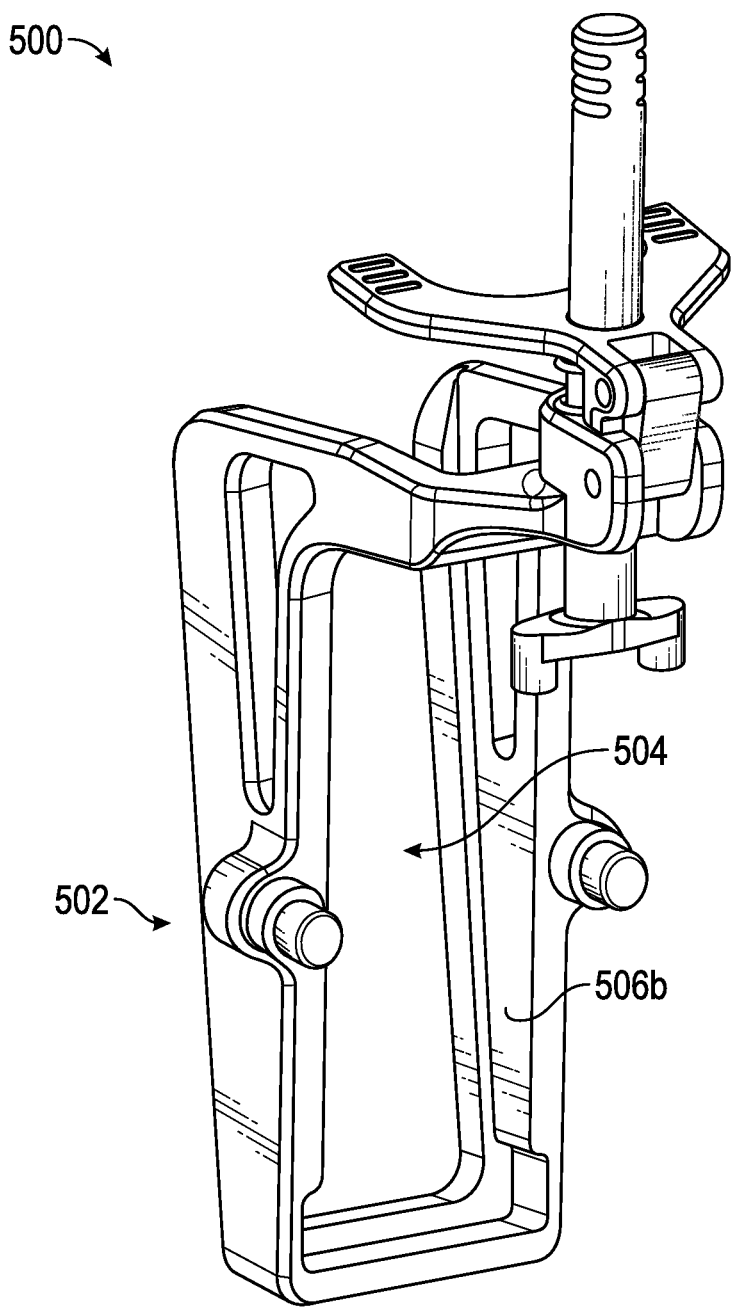

FIGS. 19 and 19A show another example of a guide assembly 500. The guide assembly 500 can include an alternative track system along the frame 502 within the opening 504. According to the example of FIGS. 19 and 19A the track system can comprise a recess in 506A (FIG. 19) and 506B (FIG. 19A) that can guide the bushing 172B (FIGS. 9A, 9B, 20A, 20B, and 20C) in a generally proximal-distal direction.

Figure 20A:
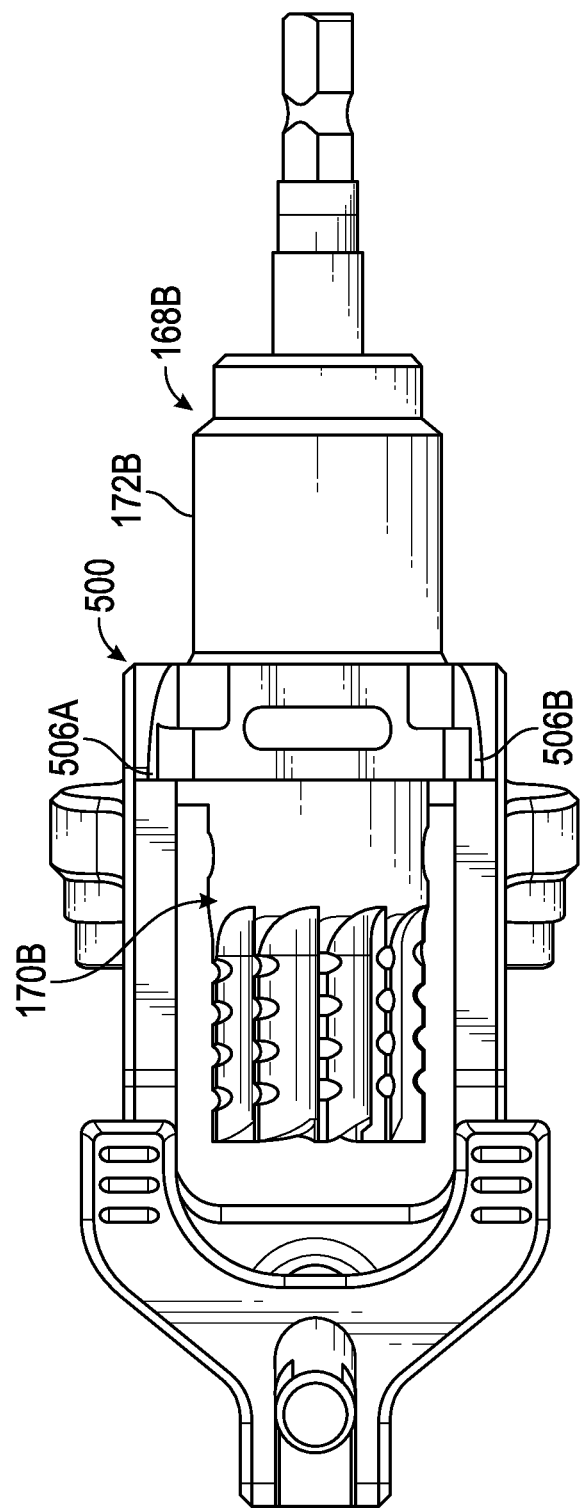
FIGS. 20A, 20B and 20C are views of the guide and the secondary guide of FIGS. 19 and 19A interacting with the first cutting tool of FIGS. 9A and 9B according to an example of the present application.
Figure 20B:
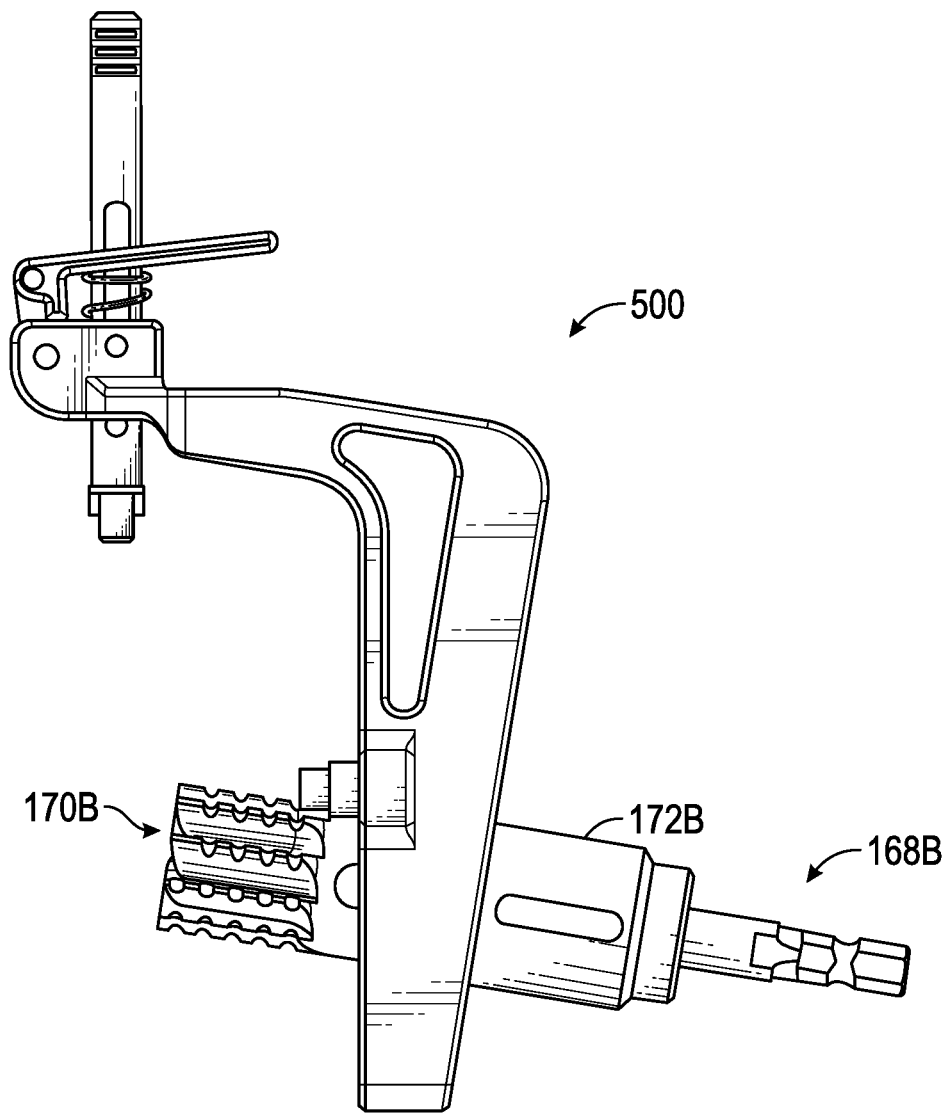
Figure 20C:
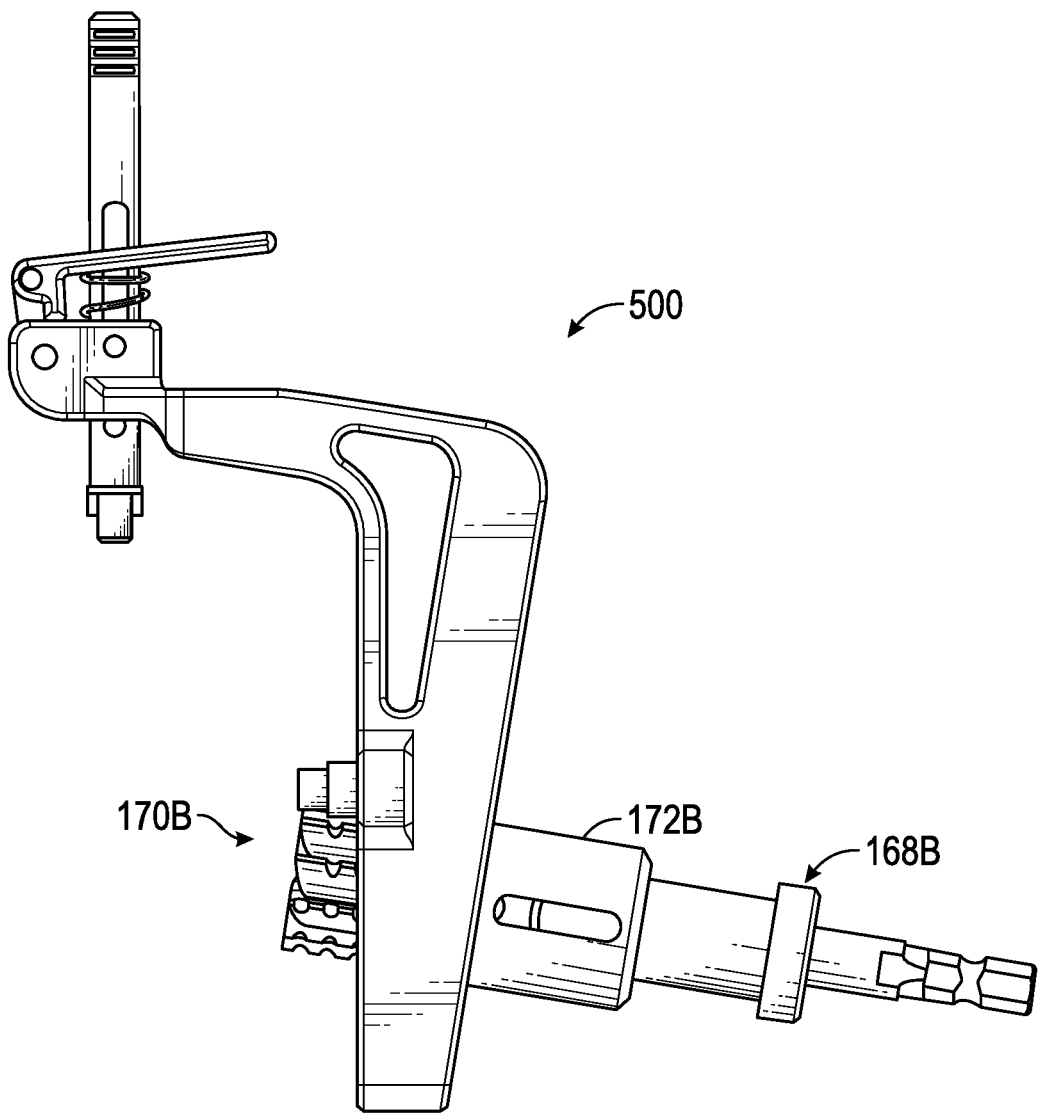

As shown in FIGS. 20A, 20B, and 20C, the guide recesses 506A and 506B (shown only in FIG. 20A) of the guide assembly 500 can be configured to only allow the second cutting tool 168B (comprising the reamer 170B and the busing 172B) to be transitioned in a generally proximal-distal direction. The reamer 170B can extend more anterior-posterior inside the reamer bushing as shown in FIG. 20B. The reamer 170B can also be retracted as shown in FIG. 20C. This extension and retraction can create a smooth linear motion during plunge action. Distal bone and/or soft tissue can be cut via reamer plunge action or milling translation in the general proximal-distal direction of the reamer 170B, with reamer body pushed as far posterior as the guide recesses 506A and 506B allow as shown in FIGS. 20A and 20B.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A system for guiding femoral bone and/or tissue removal during a knee replacement surgery, the system comprising:
a femoral component configured to engage a resected distal surface of a femur, the femoral component having a box cutout configured to provide access to a distal centrally located region of the femur, the box cutout disposed between a medial condyle, a lateral condyle and an anterior portion of the femoral component;
a femoral insert configured to be secured within the box cutout, wherein together the femoral insert and the femoral component form a trial femoral prosthesis;
a guide configured to selectively connect to the femoral component at one or more locations, the guide comprising a frame forming an enclosed opening configured to provide access to the box cutout and the distal centrally located region of the femur, wherein the frame has a curved portion such that the frame defines a first opening portion of the enclosed opening that is oriented transverse to a second opening portion of the enclosed opening;
and
a first cutting tool having a distal first portion configured to access the box cutout and the distal centrally located region of the femur via the enclosed opening, the first cutting tool having a second portion more proximally disposed than the first portion and having a larger diameter than the first portion,
wherein when the guide is connected to the femoral component, the frame is configured such that the first opening portion and the second opening portion allow the first cutting tool to access the box cutout and the distal portion of the femur from different orientations.

2. The system of claim 1, wherein the guide and the first cutting tool are configured such that insertion of the first cutting tool into the guide occurs until contact is made between the second portion of the first cutting tool and the guide, wherein the contact sets a desired access depth for the first portion of the first cutting tool relative to the guide, the desired access depth providing for removal of a desired amount of tissue in the distal centrally located region of the femur.

3. The system of claim 1, wherein the first cutting tool comprises a trephine, and wherein a proximal frame portion of the guide forms the first opening portion and includes a recessed lip configured to be engaged by the second portion of the trephine, the trephine configured to cut tissue at the distal centrally located region of the femur.

4. The system of claim 3, further comprising a second cutting tool comprising a reamer, the reamer configured to cut tissue by one or both of plunging and milling, wherein the frame forms one or more surfaces that are configured to act as a track to be traced along by the reamer when removing at least one of bone and tissue from the distal centrally located region of the femur.

5. The system of claim 1, wherein the first cutting tool comprises a reamer, the reamer configured to cut tissue by one or both of plunging and milling, wherein the frame forms one or more surfaces that are configured to act as a track to be traced along by the reamer when removing at least one of bone and tissue from the distal centrally located region of the femur.

6. The system of claim 1, wherein a proximal frame portion of the guide forms the first opening portion and includes a recessed lip configured to be engaged by the second portion of the first cutting tool, the first cutting tool configured to cut tissue at the distal centrally located region of the femur.

7. The system of claim 6, wherein the recessed lip sets a desired access depth for the first cutting tool.

8. The system of claim 1, wherein an anterior frame portion of the guide forms the second opening portion and includes at least one distal surface configured to act as a stop to set a desired access depth for a reamer.

9. The system of claim 1, wherein a first surface of the guide is spaced by the enclosed opening from a second surface of the guide, and wherein a medial-lateral distance between and a medial-lateral positioning of the first and the second surfaces of the guide corresponds to a medial-lateral distance and a medial-lateral positioning of surfaces of the medial and the lateral condyles that form the box cutout.

10. The system of claim 9, wherein a proximal-distal extent of the first and second surfaces of the guide exceeds a proximal-distal extent of the box cutout.

11. The system of claim 9, wherein the first and second surfaces of the guide are configured to act as a track to be traced along by a reamer in removing one or more of bone and soft tissue from the distal centrally located region of the femur.

12. The system of claim 1, wherein the guide selectively connects to the femoral component via a locking feature that is biased into engagement with a mating recess through an aperture in the femoral component.

13. The system of claim 1, wherein the guide further comprises a distal frame portion having at least one distal surface configured to act as a stop to set a desired access depth for a reamer.

14. A system for guiding femoral bone and/or tissue removal during a knee replacement surgery, the system comprising:
a femoral component configured to engage a resected distal surface of a femur, the femoral component having a box cutout configured to provide access to a distal centrally located region of the femur, the box cutout disposed between a medial condyle, a lateral condyle and an anterior portion of the femoral component;
a femoral insert configured to be secured within the box cutout, wherein together the femoral insert and the femoral component form a trial femoral prosthesis;
a guide configured to selectively connect to the femoral component at one or more locations, the guide comprising a frame forming an enclosed opening configured to provide access to the box cutout and the distal centrally located region of the femur,
wherein the frame has a curved portion such that the frame defines a first opening portion of the enclosed opening that is oriented transverse to a second opening portion of the enclosed opening;
and
a reamer, configured to cut tissue by one or both of plunging and milling,
wherein the frame forms one or more surfaces that are configured to act as a track to be traced along by the reamer when removing at least one of bone and tissue from the distal centrally located region of the femur, wherein when the guide is connected to the femoral component, the frame is configured such that the first opening portion and the second opening portion allow the reamer to access the box cutout and the distal portion of the femur from different orientations including a proximal-distal orientation and an anterior-posterior orientation.

15. The system of claim 14, wherein the guide further comprises a distal frame portion having at least one distal surface configured to act as a stop to set a desired access depth for the reamer.

16. The system of claim 14, wherein an anterior frame portion of the guide forms the second opening portion of the enclosed opening and includes at least one distal surface configured to act as a stop to set a desired access depth for the reamer.

17. The system claim 14, wherein the one or more surfaces of the guide comprise a first surface of the guide spaced by the enclosed opening from a second surface of the guide, and wherein a medial-lateral distance between and a medial-lateral positioning of the first and the second surfaces of the guide corresponds to a medial-lateral distance and a medial-lateral positioning of surfaces of the medial and the lateral condyles that form the box cutout.

* * * * *